(12) United States Patent
Niemeyer

(10) Patent No.: US 8,486,053 B2
(45) Date of Patent: *Jul. 16, 2013

(54) FRICTION COMPENSATION IN A MINIMALLY INVASIVE SURGICAL APPARATUS

(75) Inventor: Gunter D. Niemeyer, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 921 days.

This patent is subject to a terminal disclaimer.

(21) Appl. No.: 12/554,685

(22) Filed: Sep. 4, 2009

(65) Prior Publication Data

US 2009/0326557 A1 Dec. 31, 2009

Related U.S. Application Data

(60) Division of application No. 11/226,080, filed on Sep. 13, 2005, now Pat. No. 7,713,263, which is a continuation of application No. 10/864,273, filed on Jun. 8, 2004, now Pat. No. 6,974,449, which is a division of application No. 10/402,678, filed on Mar. 27, 2003, now Pat. No. 6,899,705, which is a division of application No. 09/287,513, filed on Apr. 7, 1999, now Pat. No. 6,565,554.

(51) Int. Cl.
*A61B 17/00* (2006.01)
(52) U.S. Cl.
USPC .............................................................. 606/1
(58) Field of Classification Search
USPC .............. 600/101, 102, 114, 164, 429; 606/1, 606/136, 139, 169, 309
See application file for complete search history.

(56) References Cited

U.S. PATENT DOCUMENTS

| | | | |
|---|---|---|---|
| 3,818,284 | A | 6/1974 | Deversterre et al. |
| 3,905,215 | A | 9/1975 | Wright |
| 4,499,905 | A | 2/1985 | Greenberg et al. |
| 4,499,906 | A | 2/1985 | Wohlgemuth et al. |
| 5,419,335 | A | 5/1995 | Hartmann et al. |
| 5,581,166 | A | 12/1996 | Eismann et al. |
| 5,593,415 | A | 1/1997 | Adrian |
| 5,767,648 | A | 6/1998 | Morel et al. |
| 5,791,908 | A | 8/1998 | Gillio |
| 5,808,665 | A | 9/1998 | Green |
| 5,855,583 | A | 1/1999 | Wang et al. |
| 5,990,869 | A | 11/1999 | Kubica et al. |
| 6,212,443 | B1 | 4/2001 | Nagata et al. |

(Continued)

FOREIGN PATENT DOCUMENTS

| | | |
|---|---|---|
| WO | WO-9729690 | 8/1997 |
| WO | WO-9743942 | 11/1997 |
| WO | WO-9743943 | 11/1997 |

OTHER PUBLICATIONS

Baumann, Roger, "Haptic Interface for Virtual Reality Based Laparoscopic Surgery Training Environment," Theses No. 1734 Ecole Pholytechnique Federale de Lausanne, 1997, 104 Total Pages.

(Continued)

*Primary Examiner* — Aaron Roane

(57) ABSTRACT

Devices, systems, and methods for compensate for friction within powered automatic systems, particularly for telesurgery and other telepresence applications. Dynamic friction compensation may comprise applying a continuous load in the direction of movement of a joint, and static friction compensation may comprise applying alternating loads in positive and negative joint actuation directions whenever the joint velocity reading falls within a low velocity range.

3 Claims, 18 Drawing Sheets

U.S. PATENT DOCUMENTS

| | | |
|---|---|---|
| 6,245,084 B1 | 6/2001 | Mark et al. |
| 6,344,038 B1 | 2/2002 | Weber |
| 6,346,072 B1 | 2/2002 | Cooper |
| 6,450,948 B1 | 9/2002 | Matsuura et al. |
| 6,459,926 B1 | 10/2002 | Nowlin et al. |
| 6,587,750 B2 | 7/2003 | Gerbi et al. |
| 6,638,299 B2 | 10/2003 | Cox |
| 6,659,939 B2 | 12/2003 | Moll et al. |

OTHER PUBLICATIONS

Komada, Satoshi et al., "Bilateral robot hand based on estimated force feedback," IEEE Proceedings IECON 87 Cambridge MA, Nov. 3-6, 1987, pp. 602-607, vol. 2, IEEE.

Lazarevic, Zoran, "Feasibility of a Stewart Platform with Fixed Actuators as a Platform for CABG Surgery Device," 1997, 45 pages, Master's Thesis Columbia University Department of Bioengineering.

Neisius B. et al., "Robotic manipulator for endoscopic handling of surgical effectors and cameras," 1st Intl. Symposium on Medical Robotics and Computer Assisted Surgery, 1994, pp. 169-175, vol. 2.

Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited.

Vertut, Jean et al., Robot Technology: Teleoperation and Robotics Evolution and Development, 1986, vol. 3A, 332 pages, English translation Prentice-Hall, Inc., Inglewood Cliffs, NJ, USA.

FRICTION COMPENSATION IN A MINIMALLY INVASIVE SURGICAL APPARATUS

CROSS-REFERENCES TO RELATED APPLICATIONS

This is a divisional of U.S. patent application Ser. No. 11/226,080, filed on Sep. 13, 2005, which is a continuation of U.S. patent application Ser. No. 10/864,273, filed on Jun. 8, 2004 (now U.S. Pat. No. 6,974,449), which is a divisional of U.S. patent application Ser. No. 10/402,678 filed on Mar. 27, 2003 (now U.S. Pat. No. 6,899,705), which is a divisional of U.S. patent application Ser. No. 09/287,513 filed Apr. 7, 1999 (now U.S. Pat. No. 6,565,554), the full disclosures of which are incorporated herein by reference.

BACKGROUND OF THE INVENTION

The present invention is generally related to improved robotic devices and methods, particularly for telesurgery.

Minimally invasive medical techniques are aimed at reducing the amount of extraneous tissue which is damaged during diagnostic or surgical procedures, thereby reducing patient recovery time, discomfort, and deleterious side effects. Many surgeries are performed each year in the United States. A significant amount of these surgeries can potentially be performed in a minimally invasive manner. However, only a relatively small percentage of surgeries currently use these techniques due to limitations in minimally invasive surgical instruments and techniques and the additional surgical training required to master them.

Advances in minimally invasive surgical technology could dramatically increase the number of surgeries performed in a minimally invasive manner. The average length of a hospital stay for a standard surgery is significantly longer than the average length for the equivalent surgery performed in a minimally invasive manner. Thus, the complete adoption of minimally invasive techniques could save millions of hospital days, and consequently millions of dollars annually in hospital residency costs alone. Patient recovery times, patient discomfort, surgical side effects, and time away from work are also reduced with minimally invasive surgery.

The most common form of minimally invasive surgery is endoscopy. Probably the most common form of endoscopy is laparoscopy which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments.

The laparoscopic surgical instruments generally include a laparoscope for viewing the surgical field, and working tools defining end effectors. Typical surgical end effectors include clamps, graspers, scissors, staplers, and needle holders, for example. The working tools are similar to those used in conventional (open) surgery, except that the working end or end effector of each tool is separated from its handle by, e.g., an approximately 12-inch long, extension tube.

To perform surgical procedures, the surgeon passes these working tools or instruments through the cannula sleeves to a required internal surgical site and manipulates them from outside the abdomen by sliding them in and out through the cannula sleeves, rotating them in the cannula sleeves, levering (i.e., pivoting) the instruments against the abdominal wall and actuating end effectors on the distal ends of the instruments from outside the abdomen. The instruments pivot around centers defined by the incisions which extend through muscles of the abdominal wall. The surgeon monitors the procedure by means of a television monitor which displays an image of the surgical site via a laparoscopic camera. The laparoscopic camera is also introduced through the abdominal wall and into the surgical site. Similar endoscopic techniques are employed in, e.g., arthroscopy, retroperitoneoscopy, pelviscopy, nephroscopy, cystoscopy, cisternoscopy, sinoscopy, hysteroscopy, urethroscopy, and the like.

There are many disadvantages relating to current minimally invasive surgical (MIS) technology. For example, existing MIS instruments deny the surgeon the flexibility of tool placement found in open surgery. Most current laparoscopic tools have rigid shafts and difficulty is experienced in approaching the worksite through the small incision. Additionally, the length and construction of many endoscopic instruments reduces the surgeon's ability to feel forces exerted by tissues and organs on the end effector of the associated tool. The lack of dexterity and sensitivity of endoscopic tools is a major impediment to the expansion of minimally invasive surgery.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism or the like, to manipulate surgical instrument movements rather than directly holding and moving the tools by hand. In such a telesurgery system, the surgeon is typically provided with an image of the surgical site at the remote location. While viewing typically a three-dimensional image of the surgical site on a suitable viewer or display, the surgeon performs the surgical procedures on the patient by manipulating master control devices at the remote location, which control the motion of servomechanically operated instruments.

The servomechanism used for telesurgery will often accept input from two master controllers (one for each of the surgeon's hands), and may include two robotic arms. Operative communication between master control and an associated arm and instrument is achieved through a control system. The control system typically includes at least one processor which relays input commands from a master controller to an associated arm and instrument and from the arm and instrument assembly to the associated master controller in the case of, e.g., force feedback.

One objective of the present invention is to provide improved surgical techniques. Another objective is to provide improved robotic devices, systems, and methods. More specifically, it is an object of this invention to provide a method of compensating for friction in a minimally invasive surgical apparatus. It is a further object of the invention to provide a control system incorporating such a method of compensating for friction.

BRIEF SUMMARY OF THE INVENTION

The present invention provides improved devices, systems, and methods for compensating for friction within powered automatic systems, particularly for telesurgery and other telepresence applications. The invention allows uninhibited manipulation of complex linkages, enhancing the precision and dexterity with which jointed structures can be moved. This enhanced precision is particularly advantageous when applied to the robotic surgical systems now being developed. The friction compensation systems of the present invention address static friction (typically by applying a continuous load in the direction of movement of a joint) and the often more problematic static friction (generally by applying alternating loads in positive and negative joint actuation directions). The invention can accommodate imprecise velocity measurements by applying an oscillating load whenever the joint velocity reading falls within a low velocity range. Preferably, the oscillating load is insufficient to move the joint without additional input, and significantly reduces the break away input required to initiate movement. In the exemplary embodiment, a duty cycle of the oscillating load varies, favoring the apparent direction of movement of a velocity reading. The amplitude of the duty cycle may also vary, typically increasing as the velocity reading approaches zero.

In a first aspect, the invention provides a method of compensating for friction in an apparatus. The apparatus has at least one component that is selectively moveable in a positive component direction, and in a negative component direction. An actuator is operatively connected to the component. The method includes obtaining a component velocity reading, and defining a velocity reading region extending between a selected negative velocity reading and a selected positive velocity reading. A duty cycle is generated so that the duty cycle has a distribution between a positive duty cycle magnitude (corresponding to a friction compensation force in the positive component direction) and a negative duty cycle magnitude (corresponding to a friction compensation force in the negative component direction). The distribution is determined by the component velocity reading when it is within the velocity reading region. The actuator is loaded with a load defined by the duty cycle signal.

Preferably, the duty cycle signal will have a continuous positive duty cycle magnitude (which corresponds to the friction compensation force in the positive direction) when the component velocity reading is greater than the selected positive velocity reading. Similarly, the duty cycle signal will have a continuous negative duty cycle magnitude (corresponding to the friction compensation force in the negative component direction) when the component velocity reading is less than the selected negative velocity reading.

In the exemplary embodiment, the distribution of the duty cycle between the positive and negative magnitudes is proportional to the component velocity reading positioned within the velocity reading region. The positive and negative duty cycle magnitudes may take a gravity compensation model into account. Such a gravity compensation model may determine a variable gravity compensation force to applied to the component, for example, to artificially balance an unbalanced linkage system. Such a gravity compensated system may further benefit from a determination of a frictional compensation force corresponding to the gravity compensation force in both the positive and negative directions. In other words, in addition to compensating for friction, the method of the present invention may accommodate compensation factors for both friction and gravity, thereby simulating or approximating a friction-free balanced system, significantly enhancing the dexterity of movement which can be accommodated.

The selection of an appropriate oscillating frequency can significantly enhance friction compensation provided by these methods and systems. Hence, the frequency will preferably be selected so as to be sufficiently slow to enable the actuator (often including an electrical motor and a transmission system such as gears, cables, or the like) to respond to the directing duty cycle signal by applying the desired load, and sufficiently rapid so that the load cannot actually be felt, for example, by physically moving the joint and varying a position of an input master control device held by a surgeon. In other words, the frequency is preferably greater than the mechanical time constraints of the system, yet less than the electrical time constants of an electrical motor used as an actuator. Preferred duty cycle frequency ranges of the exemplary telesurgical system described herein are in a range from about 40 Hz to about 70 Hz, preferably being in a range from about 50 Hz to about 60 Hz. Application of these oscillating loads can facilitate movement of a joint in either a positive or negative direction, particularly when the velocity reading is so low that the system cannot accurately determine whether the system is at rest, moving slowing in a positive direction, or moving slowly in a negative direction. Once velocity measurement readings are high enough (a given measurement reading accuracies) in a positive or negative direction, a contintious (though not necessarily constant) force in the desired direction can overcome the dynamic friction of the joint.

In yet another aspect, the invention provides a method comprising manipulating an input device of a robotic system with a hand of an operator. An end effector is moved in sympathy with the manipulating step using a servomechanism of the robotic system. A velocity reading is obtained from a joint of the robotic system. An oscillating friction compensation load is applied on the joint when the velocity reading is within a first reading range.

Preferably, a continuous friction compensation load is applied when the reading is within a second reading range, typically above (either in the positive or negative direction) a minimum value. The continuous load can compensate for friction of the joint, and may vary so as to compensate for gravity when an orientation of the joint changes. The oscillating load similarly compensates for static friction of the joint in the positive and negative directions, at varying points along the load oscillation duty cycle. This method is particularly advantageous for compensating for friction and/or gravity in a joint of the input device for the robotic system, particularly where the oscillating load is less than a static friction of the joint so that the end effector can remain stationary in the hand of the operator.

In another aspect, the invention provides a telesurgery method comprising directing a surgical procedure by moving an input device of a telesurgery system with a hand of an operator. Tissue is manipulated by moving a surgical end effector in sympathy with the input device using a servomechanism of the telesurgery system. Static friction is compensated for in at least one joint of the robotic system by applying an oscillating load to the at least one joint when an absolute value of a velocity reading from the at least one joint is less than a velocity reading error range.

While the friction compensated joint may support the surgical end effector, it will preferably support the input device. The oscillating load is generally effected by applying a duty cycle to an actuator, and preferably by altering the duty cycle in response to the velocity reading so as to facilitate movement of the joint towards the positive orientation when the velocity reading is positive, and toward the negative orientation when the velocity reading is negative.

In yet another aspect, the invention provides a telepresence system comprising a master including an input device supported by a driven joint. A slave includes an end effector supported by a driven joint. A controller couples the master to the slave. The controller directs the end effector to move in sympathy with the input device. A sensor operatively associated with at least one of the driven joints generates a velocity reading. An actuator drivingly engages the at least one driven joint. The actuator applies an oscillating load on the joint to compensate for static friction of the joint when the velocity reading is within a low velocity range.

Preferably, the oscillating load is insufficient to move the at least one driven joint when the master remains stationary. In the exemplary embodiment, the end effector comprises a surgical end effector, and the slave is adapted to manipulate the surgical end effector within an internal surgical site through a minimally invasive surgical access.

BRIEF DESCRIPTION OF THE DRAWINGS

The invention will now be described, by way of example, and with reference to the accompanying diagrammatic drawings, in which.

DETAILED DESCRIPTION OF THE INVENTION

This application is related to the following patents and patent applications, the full disclosures of which are incorporated herein by reference: PCT International Application No. PCT/US98/19508, entitled "Robotic Apparatus", filed on Sep. 18, 1998; U.S. Application Ser. No. 60/111,713, entitled "Surgical Robotic Tools, Data Architecture, and Use", filed on Dec. 8, 1998; U.S. Application Ser. No. 60/111,711, entitled "Image Shifting for a Telerobotic System", filed on Dec. 8, 1998; U.S. Application Ser. No. 60/111,714, entitled "Stereo Viewer System for Use in Telerobotic System", filed on Dec. 8, 1998; U.S. Application Ser. No. 60/111,710, entitled "Master Having Redundant Degrees of Freedom", filed Dec. 8, 1998; and U.S. Pat. No. 5,808,665, entitled "Endoscopic Surgical Instrument and Method for Use", issued on Sep. 15, 1998; the full disclosures of which are incorporated herein by reference.

It is to be appreciated that although the method and control system of the invention is described with reference to a minimally invasive surgical apparatus in this specification, the application of the invention is not to be limited to this apparatus only, but can be used in any type of apparatus requiring friction compensation. Thus, the invention may find application in the fields of satellite dish tracking, handling hazardous substances, to name but two of many possible qualifying fields in which precisional movement is required. In some cases, it may be required to compensate for friction on a single part of a system such as on a master controller only.

Figure 1A:
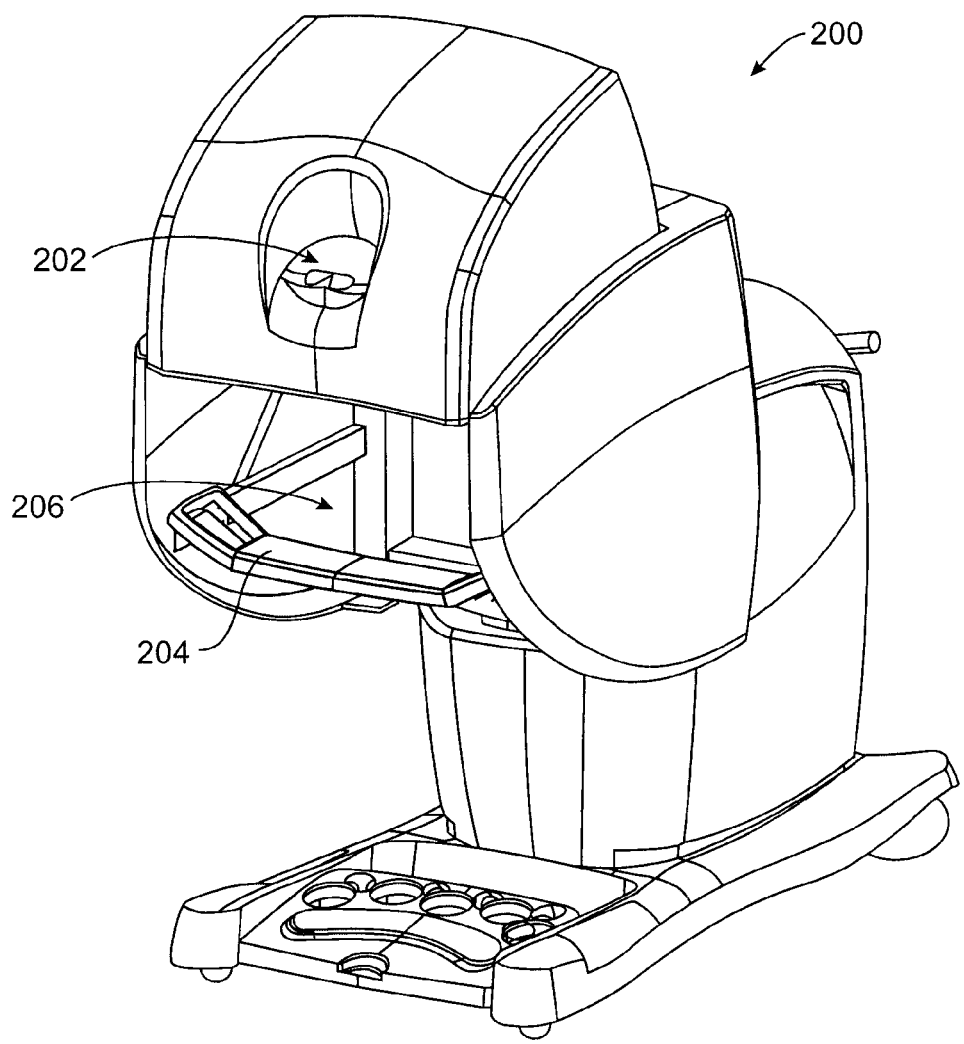
FIG. 1A shows a three-dimensional view of a control station of a telesurgical system in accordance with the invention.

Referring to FIG. 1A of the drawings, a control station of a minimally invasive telesurgical system is generally indicated by reference numeral 200. The control station 200 includes a viewer 202 where an image of a surgical site is displayed in use. A support 204 is provided on which an operator, typically a surgeon, can rest his forearms while gripping two master controls (not shown in FIG. 1A), one in each hand. The master controls are positioned in a space 206 inwardly beyond the support 204. When using the control station 200, the surgeon typically sits in a chair in front of the control station 200, positions his eyes in front of the viewer 202 and grips the master controls one in each hand while resting his forearms on the support 204.

Figure 1B:
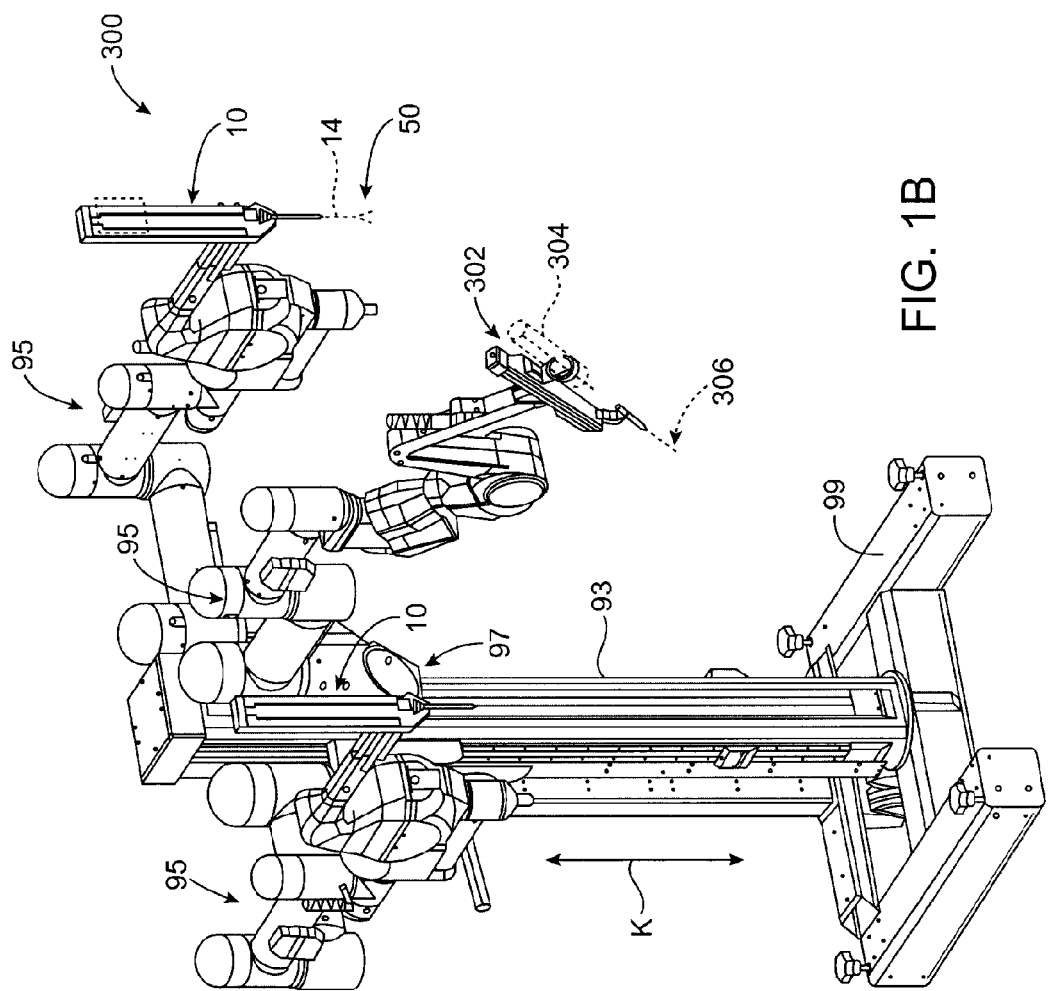
FIG. 1B shows a three-dimensional view of a cart or trolley of the telesurgical system, the cart carrying three robotically controlled arms, the movement of the arms being remotely controllable from the control station shown in FIG. 1A.

In FIG. 1B of the drawings, a cart or trolley of the telesurgical system is generally indicated by reference numeral 300. In use, the cart 300 is positioned close to a patient requiring surgery and is then normally caused to remain stationary until a surgical procedure to be performed has been completed. The cart 300 typically has wheels or castors to render it mobile. The control station 200 is typically positioned remote from the cart 300 and can be separated from the cart 300 by a great distance, even miles away.

Cart 300 typically carries three robotic arm assemblies. One of the robotic arm assemblies, indicated by reference numeral 302, is arranged to hold an image capturing device 304, e.g., an endoscope, or the like. Each of the two other arm assemblies 10,10 respectively, includes a surgical instrument 14. The endoscope 304 has a viewing end 306 at a remote end of an elongate shaft thereof. It will be appreciated that the endoscope 304 has an elongate shaft to permit it to be inserted into an internal surgical site of a patient's body. The endoscope 304 is operatively connected to the viewer 202 to display an image captured at its viewing end 306 on the viewer 202. Each robotic arm assembly 10,10 is operatively connected to one of the master controls. Thus, movement of the robotic arm assemblies 10,10 is controlled by manipulation of the master controls. The instruments 14 of the robotic arm assemblies 10, 10 have end effectors which are mounted on working ends of elongate shafts of the instruments 14. It will be appreciated that the instruments 14 have elongate shafts to permit the end effectors to be inserted into an internal surgical site of a patient's body. The end effectors are orientationally moveable relative to the ends of the shafts of the instruments 14. The orientational movement of the end effectors are also controlled by the master controls.

Figure 2A:
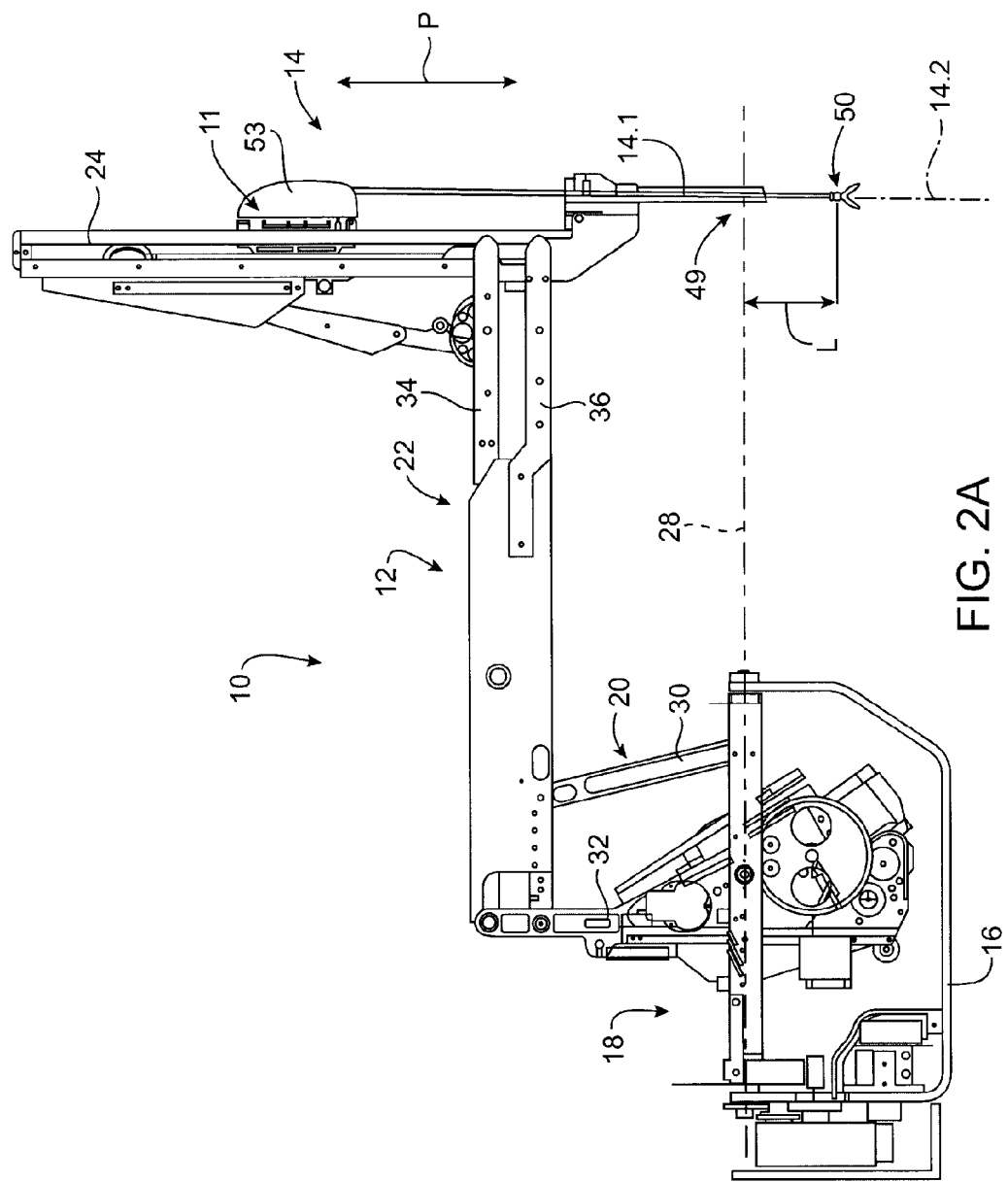
FIG. 2A shows a side view of a robotic arm and surgical instrument assembly.
Figure 2B:
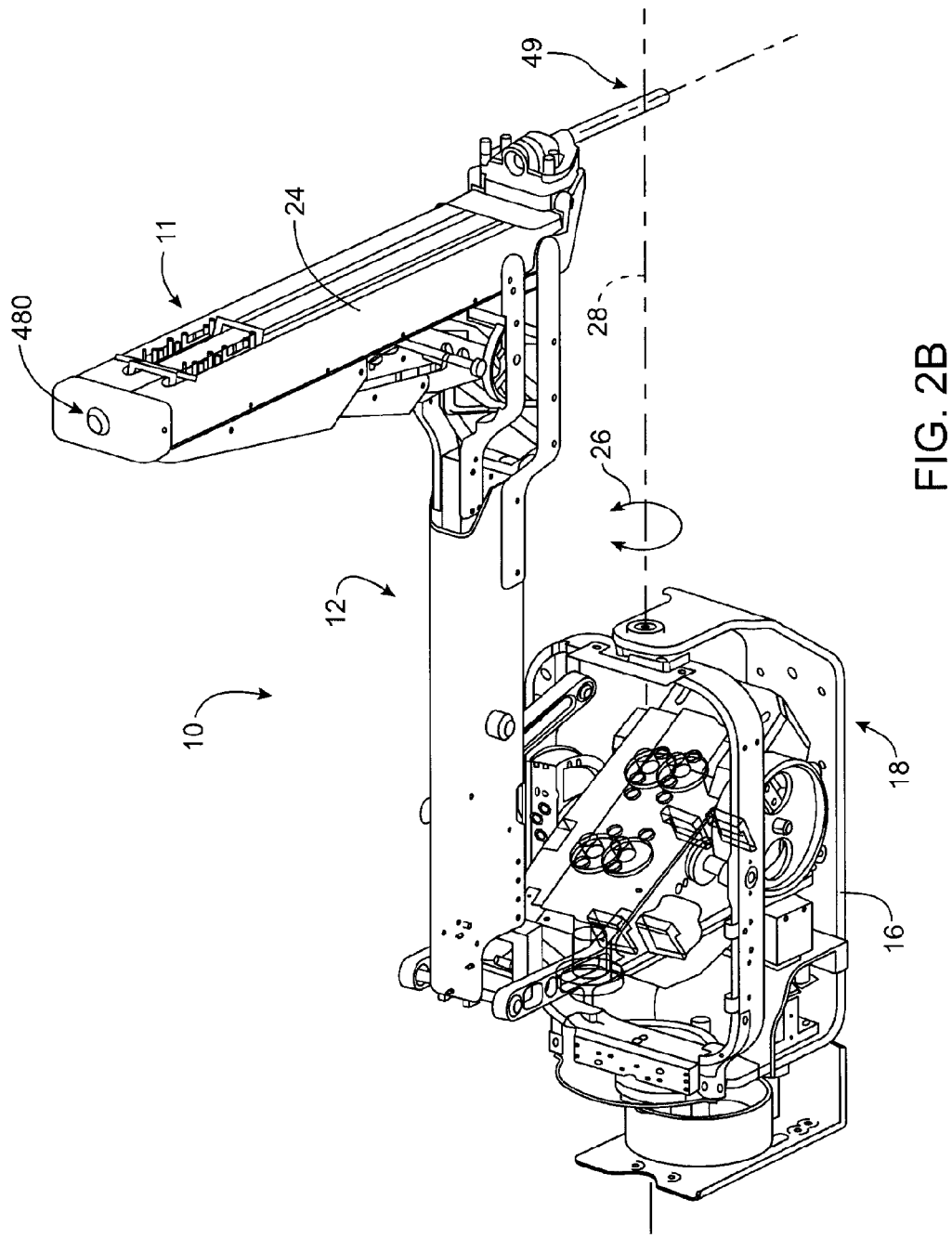
FIG. 2B shows a three-dimensional view corresponding to FIG. 2A.

In FIGS. 2A and 2B of the drawings, one of the robotic arm assemblies 10 is shown in greater detail.

Figure 3:
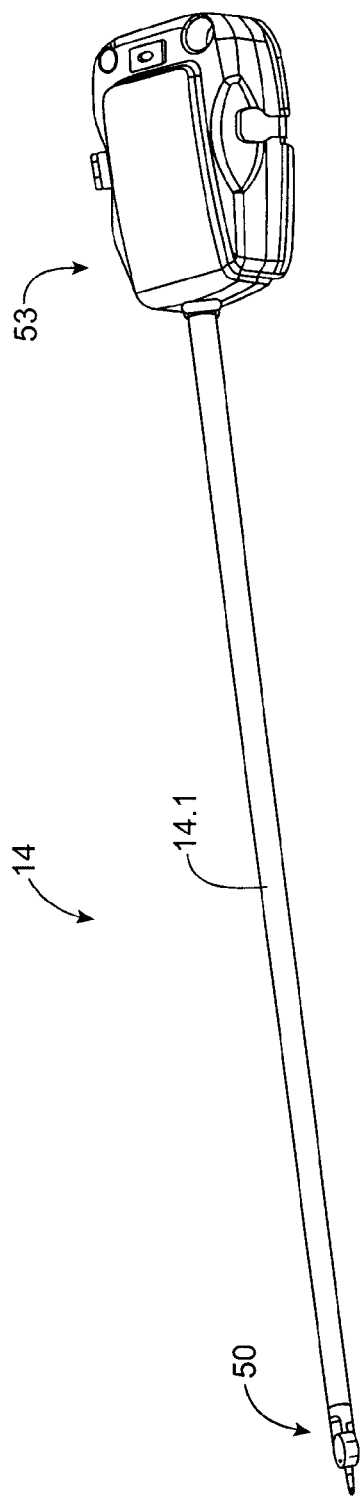
FIG. 3 shows a three-dimensional view of a surgical instrument.

The assembly 10 includes an articulated robotic arm 12, and the surgical instrument, schematically and generally indicated by reference numeral 14, mounted thereon. FIG. 3 indicates the general appearance of the surgical instrument 14 in greater detail.

In FIG. 3 the elongate shaft of the instrument 14 is indicated by reference numeral 14.1. A wrist-like mechanism, generally indicated by reference numeral 50, is located at the working end of the shaft 14.1. A housing 53, arranged releasably to couple the instrument 14 to the robotic arm 12, is located at an opposed end of the shaft 14.1. In FIG. 2A, and when the instrument 14 is coupled or mounted on the robotic arm 12, the shaft 14.1 extends along an axis indicated at 14.2. The instrument 14 is typically releasably mounted on a carriage 11, which is selectively driven to translate along a linear guide formation 24 of the arm 12 in the direction of arrows P.

The robotic arm 12 is typically mounted on a base by means of a bracket or mounting plate 16. The base is defined on the mobile cart or trolley 300, which is normally retained in a stationary position during a surgical procedure.

The robotic arm 12 includes a cradle, generally indicated at 18, an upper arm portion 20, a forearm portion 22 and the guide formation 24. The cradle 18 is pivotally mounted on the plate 16 gimbaled fashion to permit rocking movement of the cradle in the direction of arrows 26 as shown in FIG. 2B, about a pivot axis 28. The upper arm portion 20 includes link members 30, 32 and the forearm portion 22 includes link members 34, 36. The link members 30, 32 are pivotally mounted on the cradle 18 and are pivotally connected to the link members 34, 36. The link members 34, 36 are pivotally connected to the guide formation 24. The pivotal connections between the link members 30, 32, 34, 36, the cradle 18, and the guide formation 24 are arranged to constrain the robotic arm 12 to move in a specific manner. The movement of the robotic arm 12 is illustrated schematically in FIG. 4.

Figure 4:
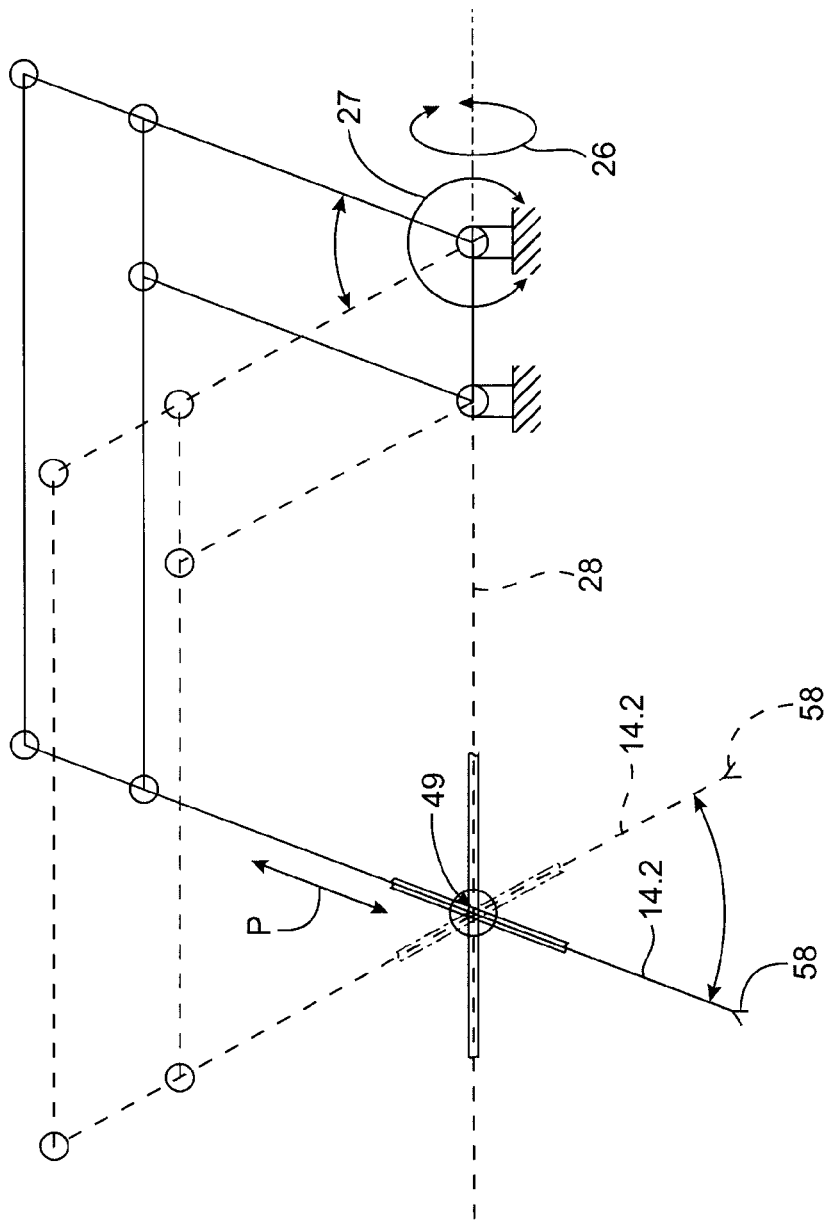
FIG. 4 shows a schematic kinematic diagram corresponding to the side view of the robotic arm shown in FIG. 2A, and indicates the arm having been displaced from one position into another position.

With reference to FIG. 4, the solid lines schematically indicate one position of the robotic arm 12 and the dashed lines indicate another possible position into which the arm 12 can be displaced from the position indicated in solid lines.

It will be understood that the axis 14.2 along which the shaft 14.1 of the instrument 14 extends when mounted on the robotic arm 12 pivots about a pivot center or fulcrum 49. Thus, irrespective of the movement of the robotic arm 12, the pivot center 49 normally remains in the same position relative to the stationary cart 300 on which the arm 12 is mounted during a surgical procedure. In use, the pivot center 49 is positioned at a port of entry into a patient's body when an internal surgical procedure is to be performed. It will be appreciated that the shaft 14.1 extends through such a port of entry, the wrist-like mechanism 50 then being positioned inside the patient's body. Thus, the general position of the mechanism 50 relative to the surgical site in a patient's body can be changed by movement of the arm 12. Since the pivot center 49 is coincident with the port of entry, such movement of the arm does not excessively effect the surrounding tissue at the port of entry.

As can best be seen with reference to FIG. 4, the robotic arm 12 provides three degrees of freedom of movement to the surgical instrument 14 when mounted thereon. These degrees of freedom of movement are firstly the gimbaled motion indicated by arrows 26, pivoting movement as indicated by arrows 27 and the linear displacement in the direction of arrows P. Movement of the arm as indicated by arrows 26, 27 and P is controlled by appropriately positioned actuators, e.g., electrical motors, which respond to inputs from an associated master control selectively to drive the arm 12 to positions as dictated by movement of the master control. Appropriately positioned sensors, e.g., encoders, potentiometers, or the like, are provided on the arm to enable a control system of the minimally invasive telesurgical system to determine joint positions.

Thus, by controlling movement of the robotic arm 12, the position of the working end of the shaft 14.1 of the instrument 14 can be varied at the surgical site by the surgeon manipulating the associated master control while viewing the responsive positional movement of the working end of the shaft 14.1 in the viewer 202.

Figure 5:
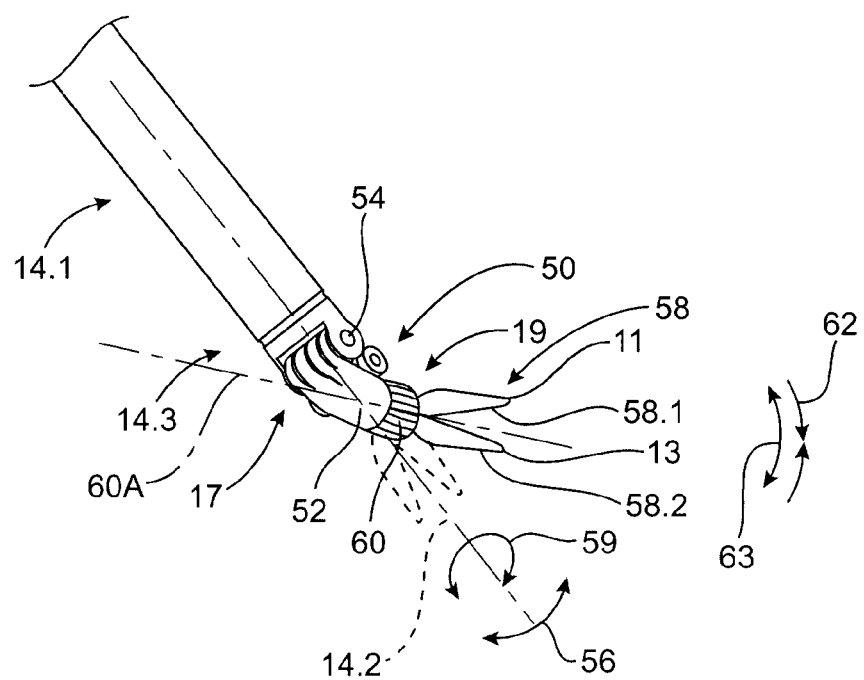
FIG. 5 shows, at an enlarged scale, a wrist member and end effector of the surgical instrument shown in FIG. 3, the wrist member and end effector being movably mounted on a working end of a shaft of the surgical instrument.

Referring now to FIG. 5 of the drawings, the wrist-like mechanism 50 will now be described in greater detail. In FIG. 5, the working end of the shaft 14.1 is indicated at 14.3. The wrist-like mechanism 50 includes a wrist member 52. One end portion of the wrist member 52 is pivotally mounted in a clevis, generally indicated at 17, on the end 14.3 of the shaft 14.1 by means of a pivotal connection 54. The wrist member 52 can pivot in the direction of arrows 56 about the pivotal connection 54. An end effector, generally indicated by reference numeral 58, is pivotally mounted on an opposed end of the wrist member 52. The end effector 58 is in the form of, e.g., a clip applier for anchoring clips during a surgical procedure. Accordingly, the end effector 58 has two parts 58.1, 58.2 together defining a jaw-like arrangement. It will be appreciated that the end effector can be in the form of any required surgical tool having two members or fingers which pivot relative to each other, such as scissors, pliers for use as needle drivers, or the like. Instead, it can include a single working member, e.g., a scalpel, cautery electrode, or the like. When a tool other than a clip applier is required during the surgical procedure, the tool 14 is simply removed from its associated arm and replaced with an instrument bearing the required end effector, e.g., a scissors, or pliers, or the like.

The end effector 58 is pivotally mounted in a clevis, generally indicated by reference numeral 19, on an opposed end of the wrist member 52, by means of a pivotal connection 60. It will be appreciated that free ends 11, 13 of the parts 58.1, 58.2 are angularly displaceable about the pivotal connection 60 toward and away from each other as indicated by arrows 62, 63. It will further be appreciated that the members 58.1, 58.2 can be displaced angularly about the pivotal connection 60 to change the orientation of the end effector 58 as a whole, relative to the wrist member 52. Thus, each part 58.1, 58.2 is angularly displaceable about the pivotal connection 60 independently of the other, so that the end effector 58, as a whole, is angularly displaceable about the pivotal connection 60 as indicated in dashed lines in FIG. 5. Furthermore, the shaft 14.1 is rotatably mounted on the housing 53 for rotation as indicated by the arrows 59. Thus, the end effector 58 has three orientational degrees of freedom of movement relative to the working end 14.3, namely, rotation about the axis 14.2 as indicated by arrows 59, angular displacement as a whole about the pivot 60 and angular displacement about the pivot 54 as indicated by arrows 56. It will be appreciated that orientational movement of the end effector 58 is controlled by appropriately positioned electrical motors which respond to inputs from the associated master control to drive the end effector 58 to a desired orientation as dictated by movement of the master control. Furthermore, appropriately positioned sensors, e.g., encoders, or potentiometers, or the like, are provided to permit the control system of the minimally invasive telesurgical system to determine joint positions.

Figure 7:
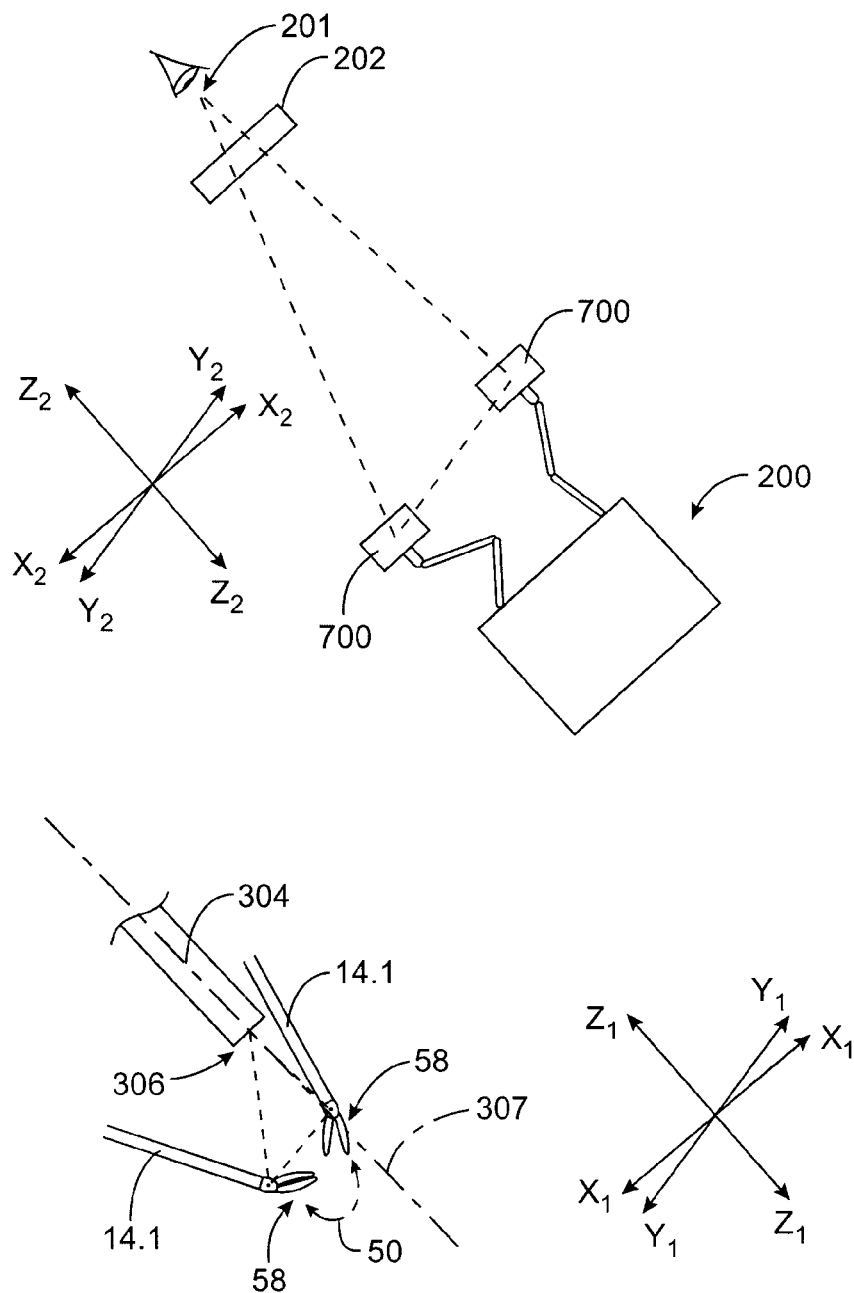
FIG. 7 shows a schematic three-dimensional drawing indicating the positions of the end effectors relative to a viewing end of an endoscope and the corresponding positions of master control input devices relative to the eyes of an operator, typically a surgeon.

In use, and as schematically indicated in FIG. 7 of the drawings, the surgeon views the surgical site through the viewer 202. The end effector 58 carried on each arm 12 is caused to perform movements and actions in response to movement and action inputs of its associated master control. It will be appreciated that during a surgical procedure responsive movement of the robotic arm 12 on which the surgical instrument 14 is mounted causes the end effector to vary its position at the surgical site whilst responsive movement of the end effector relative to the end 14.3 of the shaft 14.1 causes its orientation to vary relative to the end 14.3 of the shaft 14.1. Naturally, during the course of the surgical procedure the orientation and position of the end effector is constantly changing in response to master control inputs. The images of the end effectors 58 are captured by the endoscope together with the surgical site and are displayed on the viewer 202 so that the surgeon sees the positional and orientational movements and actions of the end effectors 58 as he or she controls such movements and actions by means of the master control devices.

Figure 6A:
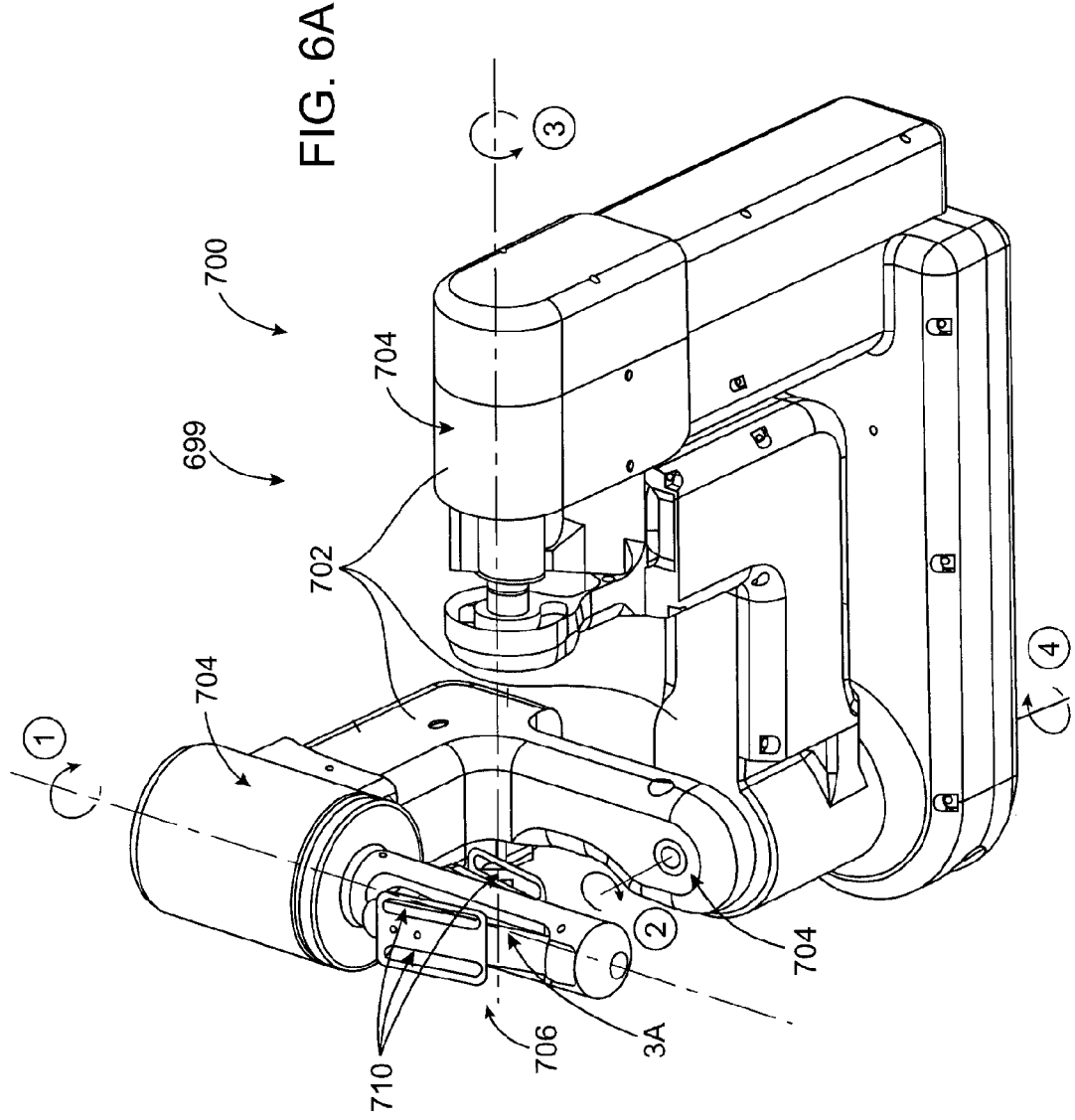
FIG. 6A shows a three-dimensional view of a hand-held part or wrist gimbal of a master control device of the telesurgical system.
Figure 6B:
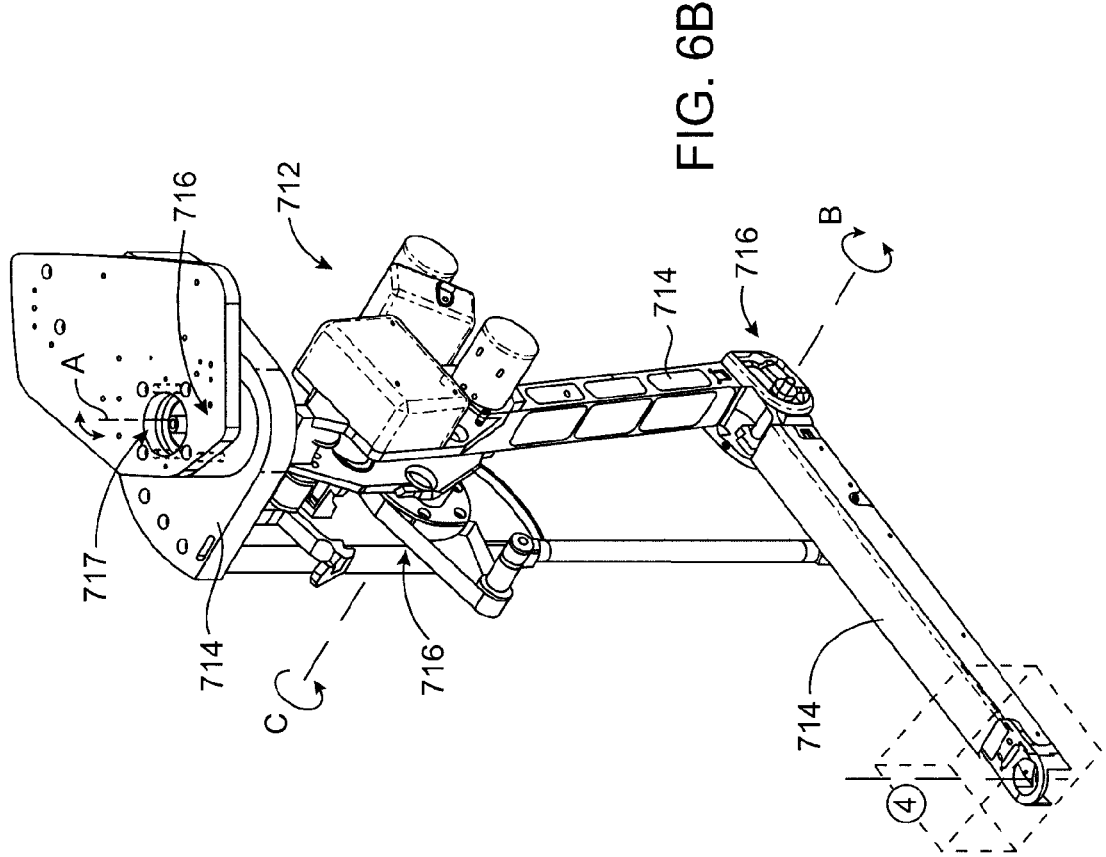
FIG. 6B shows a three-dimensional view of an articulated arm portion of the master control device on which the hand-held part of FIG. 6A is mounted in use.
Figure 6C:
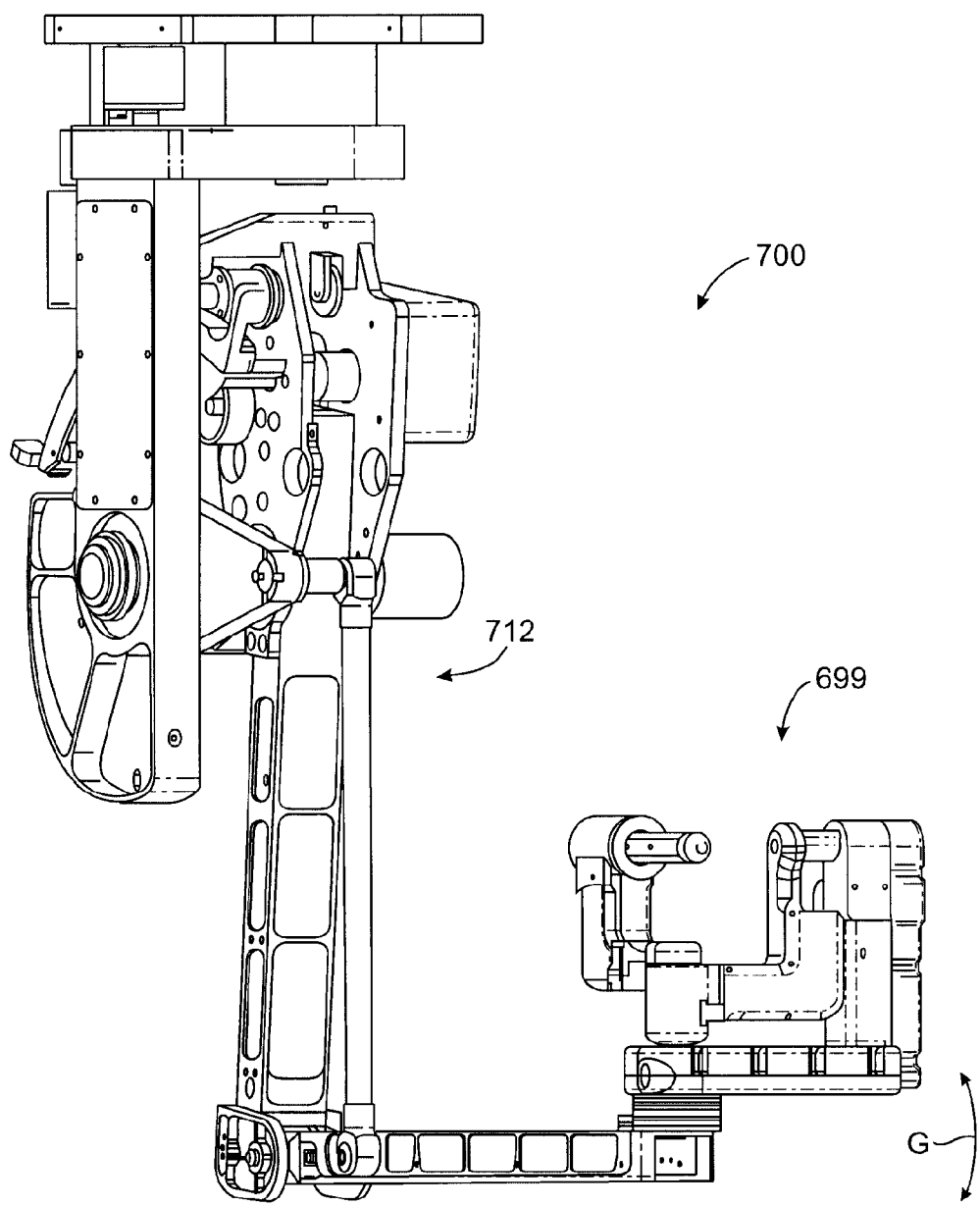
FIG. 6C shows a three-dimensional view of the master control device, the wrist gimbal of FIG. 6A shown in a mounted condition on the articulated arm portion of FIG. 6B.

An example of one of the master control devices is shown in FIG. 6C and is generally indicated by reference numeral 700. The master control 700 includes a hand-held part or wrist gimbal 699 and an articulated arm portion 712. The hand-held part 699 will now be described in greater detail with reference to FIG. 6A.

The part 699 has an articulated arm portion including a plurality of members or links 702 connected together by joints 704. The surgeon grips the part 699 by positioning his or her thumb and index finger over a pincher formation 706 of the part 699. The surgeon's thumb and index finger are typically held on the pincher formation 706 by straps (not shown) threaded through slots 710. The joints of the part 699 are operatively connected to electric motors to provide for, e.g., force feedback, gravity compensation, and/or the like. Furthermore, appropriately positioned sensors, e.g., encoders, or potentiometers, or the like, are positioned on each joint of the part 699, so as to enable joint positions of the part 699 to be determined by the control system.

The part 699 is mounted on the articulated arm portion 712 indicated in FIG. 6B. Reference numeral 4 in FIGS. 6A and 6B indicates the positions at which the part 699 and the articulated arm 712 are connected together. When connected together, the part 699 can displace angularly about an axis at 4.

Referring now to FIG. 6B, the articulated arm 712 includes a plurality of links 714 connected together at joints 716. Articulated arm 712 may have appropriately positioned electric motors to provide for, e.g., force feedback, gravity compensation, and/or the like. Furthermore, appropriately positioned sensors, e.g., encoders, or potentiometers, or the like, are positioned on the joints 716 so as to enable joint positions of the master control to be determined by the control system.

When the pincher formation 706 is squeezed between the thumb and index finger, the fingers of the end effector 58 close. When the thumb and index finger are moved apart the fingers 58.1, 58.2 of the end effector 58 move apart in sympathy with the moving apart of the pincher formation 706. To cause the orientation of the end effector 58 to change, the surgeon simply causes the pincher formation 706 to change its orientation relative to the end of the articulated arm portion 712. To cause the position of the end effector 58 to change, the surgeon simply moves the pincher formation 706 to cause the position of the articulated arm portion 712 to change.

The electric motors and sensors associated with each robotic arm 12 and the surgical instrument 14 mounted thereon, and the electric motors and the sensors associated with each master control device 700, namely the part 699 and the articulated arm portion 712, are operatively linked in the control system (not shown). The control system typically includes at least one processor for effecting control between master control device input and responsive robotic arm and surgical instrument output and for effecting control between robotic arm and surgical instrument input and responsive master control output in the case of, e.g., force feedback.

As can best be seen in FIG. 6C, each master control device 700 is typically mounted on the control station 200 by means of a pivotal connection, as indicated at 717. As mentioned hereinbefore, to manipulate each master control device 700, the surgeon positions his thumb and index finger over the pincher formation 706. The pincher formation 706 is positioned at a free end of the articulated arm portion of the part 699, which in turn is positioned on a free end of the articulated arm 712. It will be appreciated that the master control device 700 has a center of gravity normally removed from the vertical relative to its pivotal connection 717 on the control station 200. Thus, should the surgeon let go of the pincher formation 706, the master control device 700 would drop due to gravity. It has been found that providing the master controls 700, 700 with gravity compensation so that whenever the surgeon lets go of the pincher formations 706, 706, the master controls 700, 700 remain at their positions and orientations is beneficial. Furthermore, since performing surgical procedures involves precision movements, it is beneficial that the surgeon does not need to cope with a weighted feeling when gripping the pincher formations 706,706 of the master controls 700, 700. Thus, the control system of the telesurgical minimally invasive system is arranged to provide gravity compensation to the master control devices 700, 700. This gravity compensation can be achieved passively by use of counterbalancers, and/or springs, and/or the like, and/or actively by appropriate application of forces or torques on the motors operatively associated with each master control 700. In the present case, the gravity compensation is achieved actively by means of appropriate compensating torques on motors associated with each master control 700.

It will be appreciated that operative connection between the electrical motors and the master controls 700, 700, is typically achieved by means of transmissional components. These transmissional components typically include gear trains. Naturally, other transmissional components such as pulley and cable arrangements, and/or the like, can be used instead, or in addition. Regardless of the specific transmission used, these components will generally induce both static and dynamic friction in the telesurgical system.

It has been found that in providing gravity compensation, the gear trains between the motors and the master controls are typically under load. This increases the frictional forces between meshing gears and leads to increased friction when the master control is moved or urged to move by the surgeon.

It has been found that the increase in frictional forces, due to gravity compensation in particular, renders master control movement uncomfortable and unpleasant (and may lead to imprecise movements) due to hysteresis.

Figure 8:
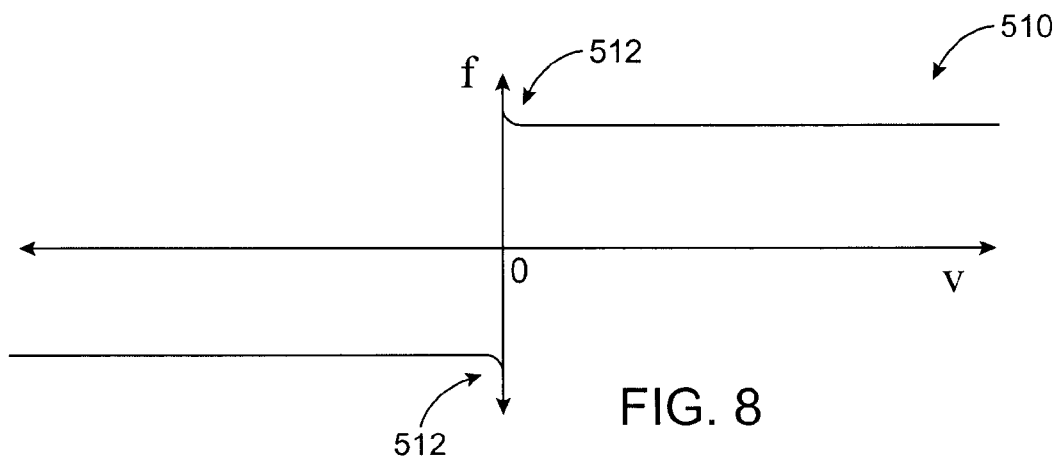
FIG. 8 shows a schematic graphical relationship between measured velocity (v) and a required force (f) to compensate for friction.

Referring to FIG. 8 of the drawings, a typical graphical relationship between velocity and a desired force for compensation of friction is indicated by reference numeral 510. Velocity is indicated on the horizontally extending axis and the required compensating frictional force is indicated on the vertically extending axis. To the left of the vertical axis a force in an arbitrary negative direction is indicated, and to the right of the vertical axis a force in an arbitrary positive direction is indicated. When movement is to be induced from a rest position, the force required to induce movement from rest is normally higher than that required to maintain movement after movement is initiated. This characteristic of friction is indicated by the opposed "spikes" at 512 in FIG. 8, and is referred to as "stiction." The spikes have been indicated in extended fashion along the velocity axis for the sake of clarity. However, it is to be appreciated that the spikes normally occur on the force axis and need not extend along the velocity axis as indicated. Note that the dynamic friction forces may not be perfectly constant, but may vary with velocity. When movement is initiated friction can readily be compensated for by applying a corresponding compensating force. However, to achieve adequate friction compensation when initiating movement from rest, or when changing direction, is more problematic.

A first friction compensation technique can best be described with reference to the following simple electromechanical system, by way of example. The example of the electromechanical system includes a motor and an articulated arm. The motor is arranged to drive the articulated arm through a transmission arrangement, e.g., a gear train, or the like. For the sake of this example, the graphical relationship between velocity and frictional force shown in FIG. 8 represents the mechanical friction in the electromechanical system as a function of velocity. It is generally desirable to compensate for this friction within the electromechanical system, as the friction can be distracting to the operator, limiting the operator's dexterity and effectiveness.

One method of compensating for friction, in particular for compensating for stiction, when the arm of the example is at rest, is to inhibit the electromechanical system from ever fully being at rest. This method includes cyclically supplying a current to the motor to prevent the electromechanical system from fully coming to rest. Thus, the motor is caused cyclically to move angularly in opposed directions. Thus a cyclical torque is supplied to the motor causing the slave to oscillate. This method is referred to as "dithering."

Although this method inhibits the system from coming to rest and thus obviates stiction when movement is to be induced from a rest position, it has been found that dithering causes vibration in the system which is uncomfortable in some applications, particularly in minimally invasive surgical procedures. Furthermore, dithering can lead to excessive wear and ultimately damage to the apparatus.

Figure 9:
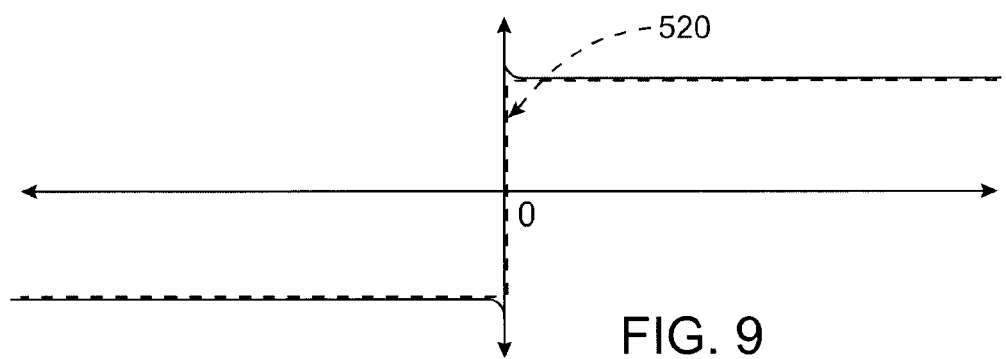
FIG. 9 shows the graphical relationship shown in FIG. 8 and one method of compensating for friction represented in dashed lines superimposed thereon.

Another method of compensating for friction is represented in FIG. 9. This method involves supplying a force of a magnitude approximating the frictional force in the system whenever it is in motion. This type of compensation is referred to as "Coulomb" friction compensation. Such a force is induced in the electromechanical system by means of motor torque of a magnitude corresponding to the frictional force required to maintain movement in a specific direction after movement is achieved in that direction. The compensating force is indicated in dashed lines by reference numeral 520 with the sign of the compensating force being determined by the sign of the measured velocity.

This method also does not make allowance for the spikes at 512. Thus, a degree of "sticking," or stiction, is still felt when movement is initiated. Since it is difficult to measure velocity accurately when a system is at rest due to measurement inaccuracies, noise, and the like, it is problematic in applying the compensating force in the correct direction. Accordingly, when movement is to be initiated in one direction from rest, the system could be measuring a velocity in the opposed direction, in which case the compensating force is applied in the same direction as the frictional force thus aggravating stiction. Should the velocity reading fluctuate at zero, a compensating force which fluctuates in opposed directions is generated which introduces unpredictable energy into the system tending to destabilize it and giving it an active "feel."

Figure 10:
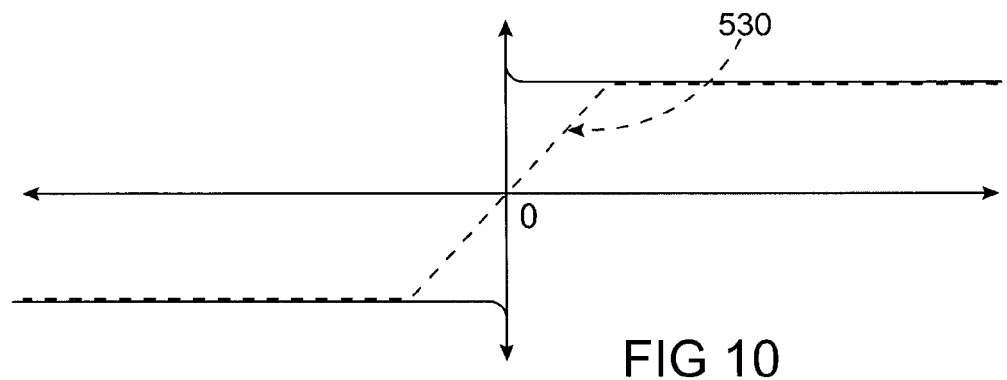
FIG. 10 shows the graphical relationship shown in FIG. 8 and another method of compensating for friction represented in dashed lines superimposed thereon.

Another method of compensating for friction is indicated in FIG. 10 in dashed lines generally indicated by reference numeral 530. This method is similar to the "Coulomb" type of compensation. However, inaccuracy in measurement around a zero velocity reading is compensated for by slanting the compensation across zero velocity. Although this method compensates for system uncertainty at zero velocity, it does not always accurately compensate for friction forces at low velocity, nor compensate for stiction when movement is to be initiated from rest. Thus, stiction is normally still present.

The preferred method of compensating for friction in accordance with the invention will now be described with particular reference to compensating for friction in a gear train of one of the master controls 700, 700 due to gravity compensation. It will be appreciated that the description which follows is by way of example only and that the method of compensating for friction is not limited to this application only, but can be readily adapted to compensate for other sources of friction such as, e.g., at pivotal joints, between components which translate relative to each other, and/or the like. Furthermore, the method can enjoy universal application to compensate for friction in any system whether to compensate for friction due to gravity compensation or merely to compensate for friction in general irrespective of the source. For example, gear train loads imposed for purposes other than gravity compensation, for example, by a controller other than gravity controller, may induce friction that can be compensated for.

The method of compensating for friction in accordance with the invention can be understood with reference to a single joint of the master control 700, for example the joint 704B in FIG. 6B of the drawings, and an electrical motor associated with that joint through a gear train. It will be appreciated that friction compensation can be provided for each joint of the master control 700.

Figure 11:
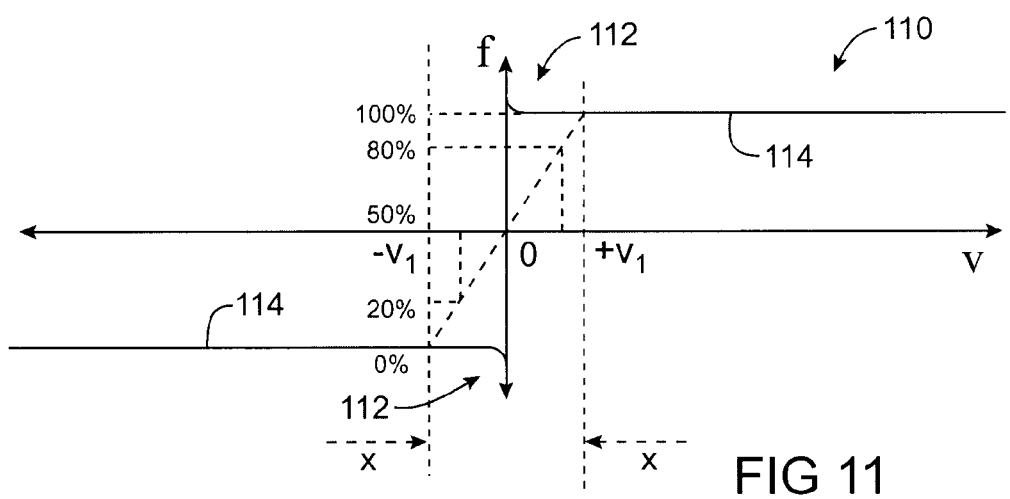
FIG. 11 shows the graphical relationship shown in FIG. 8 and further indicates detail used to exemplify a method of compensating for friction in accordance with the invention superimposed thereon.

Referring to FIG. 11 of the drawings, a graphical relationship between angular velocity (v) of the joint 704B (as measured by the control system) and the force (f) which will compensate for force in the gear train associated with the joint 704B is generally indicated by reference numeral 110. Velocity (v) extends along the horizontal axis and the required force (f) to compensate for friction in the gear train extends along the vertical axis.

It has been found that when the arm members or links 702A connected together by means of the joint 704B are in a stationary position relative to one another, and the surgeon wishes to move the master control 700 in a manner initiating movement of the arm members 702A about the joint 704B, friction is particularly evident. The reason for this is that the force required to overcome friction from a stationary position is higher than the force required to maintain movement after movement is achieved. As soon as movement is achieved, the frictional force decreases and then stays approximately constant as velocity increases. This phenomenon is schematically indicated by the opposed spikes at 112 around the zero velocity region and is termed stiction. Once movement is achieved, the frictional force requiring compensation is generally constant as indicated by the straight line portions 114.

It will be appreciated that movement of the pincher formation 706 is achieved through a plurality of joints, namely joints 704, 716 and 717. Thus, during any given pincher formation movement any one or more of the joints 704, 716, 717 may be at rest so that initiating movement about an arbitrary stationary joint or joints may be required while the pincher formation is actually moving. Thus, since there are a plurality of joints, stiction has a cumulative effect which renders precise movement of the master 700 difficult to maintain even while the pincher formation 706 is actually moving. When the pincher formation 706 is to be moved very slowly, stiction of any one or more of the joints 704, 716 and 717 is particularly problematic and renders precise movement of the pincher formation 706 (and also responsive movement by the end effector 58) difficult to maintain. In fact, smooth motion of pincher formation 706 will involve directional changes of some of the joints. This can lead to significant changes in the cumulative friction force, again rendering precise movements difficult to maintain. To overcome or compensate for stiction and the differences between static and dynamic frictional forces is particularly advantageous, since slow precise movements are often employed during a surgical procedure. Compensating for stiction and the static/dynamic differential is also particularly problematic. One reason for this is that available sensors used to measure angular velocity are not entirely accurate so that precisely measuring zero velocity of the joint when at rest is difficult. Another reason is that noise may be superimposed on the sensor signal which further aggravates the problem of measuring zero velocity when the joint is at rest. Thus, when the joint is at rest, the sensors can be registering movement and, consequently, apparent velocity.

The joint can move in an arbitrary positive and an arbitrary negative direction. The velocity reading may have a negative value, a positive value, or may be fluctuating about the zero velocity reading when the joint is at rest due to the noise and measurement inaccuracies. If the velocity reading is used to determine a frictional compensation force, it is difficult to determine when and in what direction to apply the frictional force since the velocity reading does not correspond with the actual velocity of the joint particularly when the joint is at rest. Even with an accurate velocity measurement, using a sensor which accurately measures zero velocity when the joint is actually at rest, it would still be problematic to apply a frictional compensation force to compensate for stiction since it is not easy to anticipate in which of the arbitrary positive and negative directions the joint will be moved.

To overcome these problems, and to compensate for stiction in particular whilst accommodating measurement inaccuracies, a velocity region indicated between the arrows X-X is chosen, such that if the velocity reading is within this region, a cyclical torque, varying in a positive and a negative direction is supplied to the motor so that irrespective of the direction in which movement is to be initiated from rest, a friction compensation torque is provided at least part of the time. This will be described in greater detail below.

The indicated velocity region X-X can be chosen based on measurement accuracy such that outside the region the joint is actually moving whilst inside the region the joint could either be moving very slowly in either direction or may be stationary. Outside the region X-X, it is assumed that the velocity reading does indicate joint movement in a correct direction and that movement has been initiated. A uniform compensating torque is then applied corresponding with the constant friction experienced when movement is achieved, as will be described in greater detail herein below.

Still referring to FIG. 11 of the drawings, the control system of the invention is arranged to generate compensating values determined by the velocity reading within the region X-X. This can best be explained by means of the slanted dashed line in FIG. 11. The slanted dashed line DL extends between opposed intersections of the chosen velocity reading region X-X, and the required force for compensating for friction. Naturally, the slanted line need not be linear but could be rounded at its corners, and/or the like. Furthermore, the width of the region between X-X can be tailored to suit the system friction characteristics.

The friction compensating force values along dashed line DL can be represented as percentages for generating a duty cycle appropriate to a measured velocity. Should the velocity reading be at +v1 a force value of 100% is generated. Similarly, if the velocity reading is at −v1, a value of 0% is generated. In similar fashion a specific value ranging between 0% and 100% is generated depending upon the measured velocity reading position between +v1 and −v1.

Figure 12:
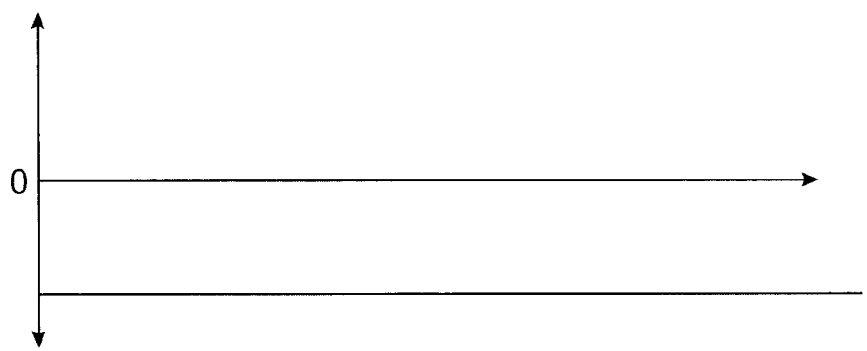
FIGS. 12 to 16 show different duty cycle distributions determined by values derived from velocity measurements indicated in FIG. 11.

The value thus generated can be used to determine a duty cycle signal distribution between the arbitrary positive and the arbitrary negative direction of movement about the joint 704B. Thus, where a value of 0% is generated, the reading then being negative, in other words, in an arbitrary negative direction, a duty cycle as indicated in FIG. 12 is generated. The distribution of the duty cycle in FIG. 12 is correspondingly fully negative, or 100% negative. The region X-X can be chosen such that at this point, taking noise and measurement inaccuracies into account, the master may be either about to actually move in the negative direction or may already be moving in the negative direction.

Figure 13:
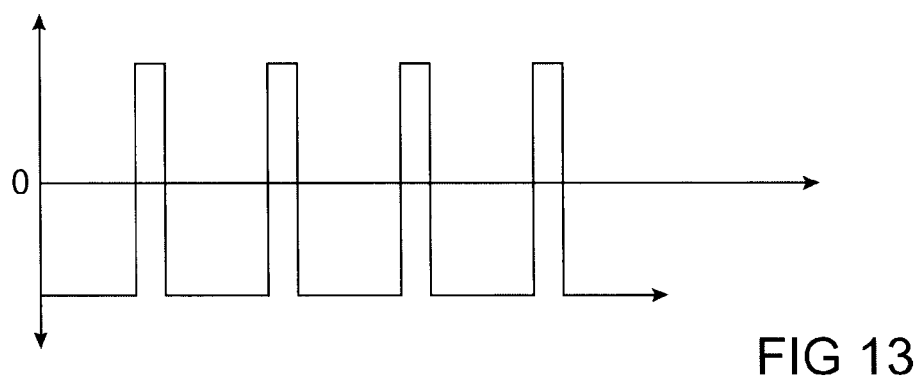

Similarly, should a value of 20% be generated, for example, a duty cycle as indicated in FIG. 13 is generated. The distribution of the duty cycle in FIG. 13 is correspondingly 20% positive and 80% negative.

Figure 14:
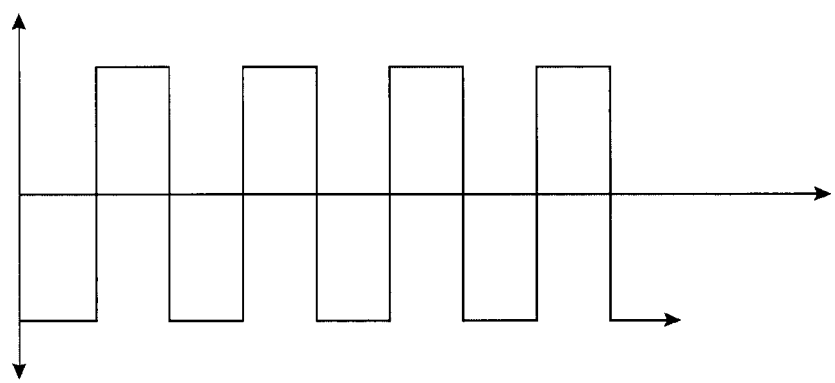

Should a value of 50% be generated, a duty cycle as indicated in FIG. 14 is generated. The distribution of the duty cycle in FIG. 14 is correspondingly 50% positive and 50% negative.

Figure 15:
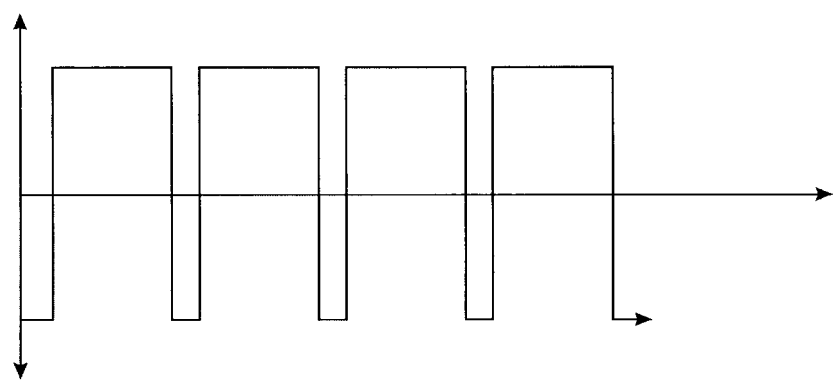

Similarly, should a value of 80% be generated, a duty cycle as indicated in FIG. 15 is generated. The distribution of the duty cycle in FIG. 15 is correspondingly 80% positive and 20% negative.

Figure 16:

In the case where a value of 100% is generated, a duty cycle as indicated in FIG. 16 is generated. The distribution of the duty cycle in FIG. 16 is correspondingly fully positive, or 100% positive. At this point, taking noise and measurement inaccuracies into account, the master can be either about to actually move in the positive direction or may already be moving in the positive direction.

It will be appreciated that the duty cycles shown need not necessarily have generally rectangular waveforms.

It will further be appreciated that when the joint is at rest, the velocity reading is typically fluctuating within the X-X region so that the duty cycle distribution is continually varying.

The method of compensating for friction will now be described in further detail with reference to FIG. 17.

Figure 17:
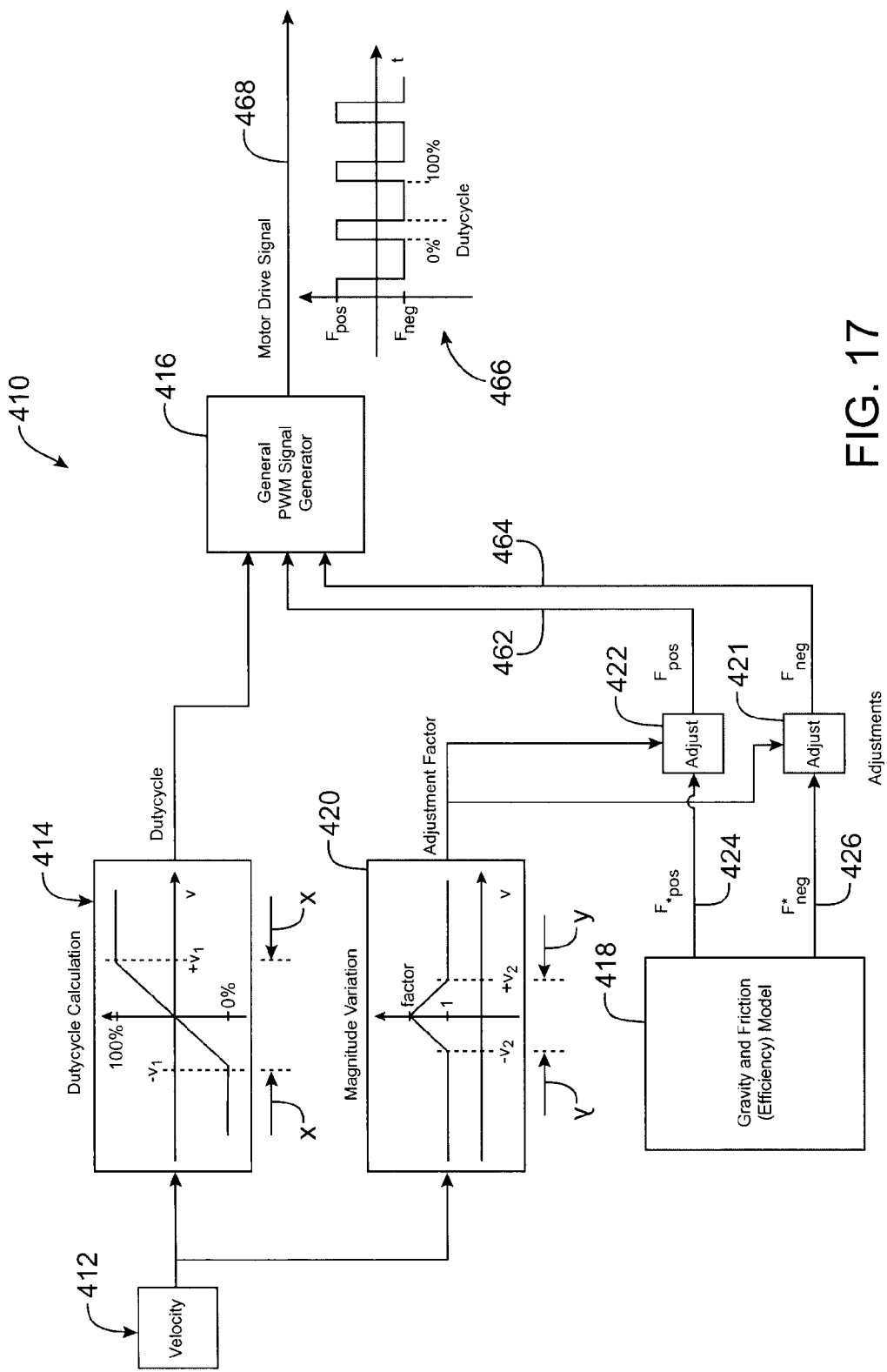
FIG. 17 shows an algorithm representing an overview of the method of compensating for friction in accordance with the invention.

In FIG. 17, a block diagram indicating steps corresponding to the method of compensating for friction in accordance with the invention is generally indicated by reference numeral 410.

The velocity readings as described above are indicated at 412. The compensating values determined from the velocity readings is indicated at 414. The compensating values are input to a duty cycle generator such as a PWM generator at 416. The resultant duty cycle signal distribution is Output from the PWM generator.

It will be appreciated that the steps from 412 to 416 are used to determine only the percentage distribution of the duty cycle signal between the arbitrary negative and positive joint movement directions. This determination is directly related to the velocity measurements between arrows XX. The determination of the amplitude or magnitude of the duty cycle signal will now be described.

Figure 20:
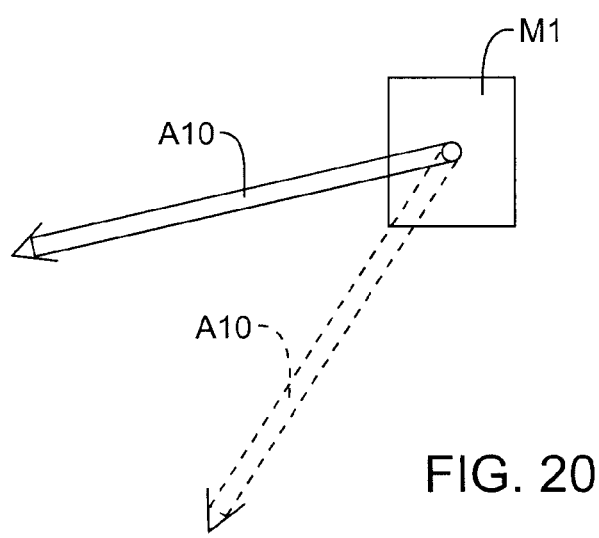
FIG. 20 shows a schematic diagram exemplifying a required gravity compensating force on a master control and how the gravity compensating force and consequently also frictional force, varies depending on master control position.

As mentioned earlier, the control system compensates for gravity. The master control 700 is moveable about a pivot at 717 and the pincher formation 706 is connected to the pivot 717 through the joints 704, 716 and the intervening arm members. The master control 700 as a whole is thus displaceable about the pivot 717. A horizontal component of the center of gravity varies as the pincher formation 706 is displaced. Accordingly, the torque supplied to an electrical motor operatively associated with the master control 700 and which balances and compensates for gravity also varies. Thus, the gravity compensating torque on the electrical motor is determined in part by the position of the center of gravity. This is indicated schematically in FIG. 20 of the drawings by way of example. In FIG. 20, it can be seen that the torque required on a motor M1 to hold an arm A10 in a position as indicated in solid lines to compensate for gravity is greater than that required to hold the arm in the position indicated in dashed lines. A similar principal applies for each joint of the master control 700. Naturally, the higher the gravity compensating torque supplied to the motor, the higher the transmission loading on the associated gear train and therefor the higher the frictional force and vice versa.

Each joint 704, 716, 717 may have an actuator, e.g., electric motor, operatively associated therewith to provide for, e.g., force feedback. Furthermore, for each joint employing gravity compensation, a corresponding gravity compensating torque is supplied to the motor operatively associated therewith. The gravity compensation torque magnitude varies depending on master control position. The motor operatively associated with each joint employing gravity compensation can be provided with a friction compensation torque in accordance with the method of the invention. The friction compensation torque magnitude applied to a particular joint varies in accordance with the gravity compensation torque. It will be appreciated that the effects of friction can be negligible on some of the joints. Hence, friction compensation may not be provided for all joints of the master and/or slave.

The friction compensation loads induced by the gravity compensation system need not, and generally will not, be applied separately. The exemplary friction compensation system described herein incorporates the gravity model, so that the gravity compensation torques become part of the load applied by the friction compensation system. Alternatively, separate gravity compensation and friction compensation loads might be maintained.

Referring once again to FIG. 17 of the drawings, a gravity compensating model is indicated at 418 whereby gravity compensation forces for the joints requiring gravity compensation are determined. For each of the joints 704, 716, 717 employing gravity compensation, the gravity compensation model determines the torque which can hold the part of the master control 700 extending from that joint in the direction of the pincher formation 706 in a stationary position. Naturally, this torque varies for each joint in sympathy with positional variation of that joint as the master control 700 is moved from one position to a next position.

Figure 18:
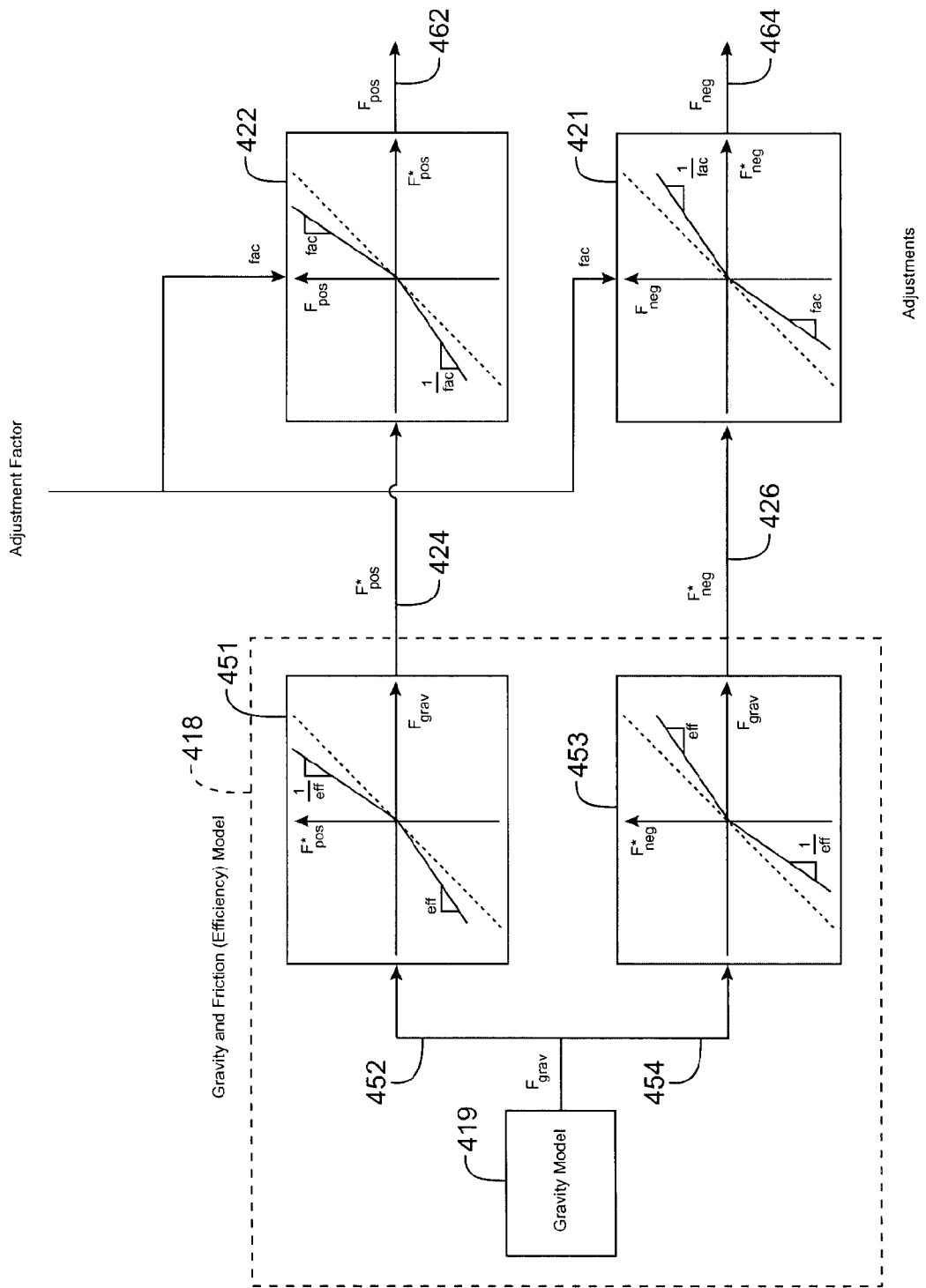
FIG. 18 shows further detail of the algorithm shown in FIG. 17 relating to gravity compensation.

Referring now to FIG. 18 of the drawings, the gravity and friction (efficiency) model 418 will now be described in greater detail. From the gravity model, indicated at 419, the magnitude of a desired gravity compensating force for the joint, e.g., joint 704B, is determined. The gravity compensating force is then forwarded to a friction compensation determining block 451 for determining friction compensation in the arbitrary positive joint movement direction as indicated by line 452. The gravity compensation force is also forwarded to a friction compensation determining block 453 for determining friction compensation in the arbitrary negative joint movement direction as indicated by line 454.

In the block 451, the magnitude of the gravity compensating force is represented along a horizontally extending axis and the corresponding required frictional compensating force for the positive joint movement direction is represented along a vertically extending axis. The corresponding frictional compensating force is determined taking the gear train efficiency into account as indicated by the lines l/eff and eff, respectively (eff being efficiency, typically less than 1).

In similar fashion, in the block 453, the magnitude of the gravity compensating force is represented along a horizontally extending axis and the corresponding required frictional compensating force for the negative joint movement direction is represented along a vertically extending axis. The corresponding frictional compensating force is determined taking the gear train efficiency into account as indicated by the lines l/eff and eff, respectively.

The magnitudes of the frictional compensating forces in respectively the positive and the negative joint movement directions determined in the blocks 451, 453 represent the magnitudes of the frictional forces in respectively the positive and negative joint movement directions after movement of the joint has been initiated. Thus, they correspond with the lines 114 in FIG. 11 of the drawings.

The magnitude of these forces are used to determine the amplitude of the duty cycle signal at 416. Thus, from 414 the percentage distribution between the arbitrary positive and negative directions were determined, and from the gravity model at 418, the magnitude or amplitude of the duty cycle signal is determined for each arbitrary positive and negative joint movement direction. It will be appreciated that these magnitudes correspond to dynamic friction compensating forces. Depending on actual joint position, these compensating forces can be dissimilar.

As mentioned earlier, overcoming friction when at rest involves a higher force than is applied to maintain movement. This characteristic of friction is compensated for at 420 when the velocity reading lies in the region Y-Y as indicated (also designated as the region between −V2 and V2). The force which can cause an object, in this case the meshing gears of the gear train, to break away from a rest position is typically some factor higher than 1, often being about 1.6 times the force to maintain movement after movement is achieved. This factor can vary depending on the application. In this case, the factor or ratio corresponds to the relationship between the force which will overcome friction in the gear train when at rest and to maintain movement in the gear train once movement has been initiated. More specifically, the ratio corresponds to the change in efficiency of the gear train when at rest versus when in motion. It will be appreciated that at 420, the ratio and effective range Y-Y can be tailored to suit a specific application. The range Y-Y could correspond with the range X-X, for example.

Referring now to 420 in greater detail, and assuming the region Y-Y corresponds with the region X-X, at 0% and 100% values, a factor of 1 is generated. At a 50% value a maximum factor is generated. Between 50% and 100% and between 50% and 0% a linear relationship between the maximum factor value, in one example 1.6, and the minimum factor value, namely 1, is established. Thus, at a value of 75% or 25% a factor of 1.3 would be generated. It will be appreciated that the relationship need not necessarily be linear.

The factor ranging between 1 and the maximum factor determined at 420 from the velocity reading is then output or forwarded to factoring or adjusting blocks at 422 and 421, respectively.

The friction compensation force for movement in the positive joint direction is input to the block 422 as indicated by line 424. In the block 422, this friction compensation value is indicated along the horizontal axis. The actual friction compensation force magnitude to compensate for stictions is indicated along the vertical axis. The value of the factor is indicated by the letters "fac." This value determines the relationship between the actual required friction compensation forces and the friction force requiring compensation when movement in the positive joint direction is achieved. Thus, the value fac determines the gradient of the lines indicated by fac and 1/fac, respectively. Naturally, when fac=1, the lines fac and 1/fac extend at 45° resulting in the actual required friction being equal to the friction requiring compensation. This corresponds with a condition in which the velocity reading is outside or equal to the outer limits of the Y-Y region. It will be appreciated that at 421, a similar adjustment takes place for friction compensation force in the negative direction.

It will be appreciated that a larger force to compensate for friction in one direction may be required than in the opposed direction, in particular because our compensation torque here indicates both friction compensation torque and gravity compensation torque. This depends on the actual position of the joint. Normally, to cause the arm member extending from the joint toward the pincher formation 706 to move in an operatively downward direction requires less friction compensation torque than moving it in an operatively upward direction. Thus, should the arbitrary positive joint movement direction correspond with an upward movement, a greater frictional compensating force is required than that in the arbitrary negative direction, and vice versa. Thus, the amplitude of the duty cycle can be higher or lower on the positive side than the negative side depending on the position of the joint, and whether the arbitrary positive joint movement direction corresponds with an upward or downward movement of the arm member extending from the joint. Indeed, the "positive" compensation load need not be in the positive direction and the "negative" load need not be in the negative direction, although the positive load will be greater than or equal to the negative load.

After the friction compensation force magnitudes have been determined in this manner, they are forwarded to the PWM signal generator at 416 as indicated by lines 462 and 464, respectively. At the PWM signal generator, the force magnitudes are combined with the duty cycle distribution signal determined at 414 to determine a resultant duty cycle signal as indicated at 466. The resultant duty cycle signal 466 is then passed from the PWM signal generator along line 468.

The duty cycle signal thus determined by the PWM signal generator 416 by combining outputs from 414, 421 and 422 is then passed to an amplifier so that the required electrical current can be passed to the electrical motor operatively associated with the joint 704B so as to generate corresponding cyclical torques on that motor.

The frequency of the duty cycle output from 416 is predetermined so as to be low enough to enable the electrical motor to respond and high enough so as not to be felt mechanically. Thus, the frequency is greater than the mechanical time constants of the system yet less than the electrical time constants of the electric motor. A suitable frequency in the exemplary telesurgical system falls in the range between 40 Hz to 70 Hz, preferably about 55 Hz.

It will be appreciated that where it is possible accurately to read zero velocity when the master control 700 is at rest, the above method of compensating for friction can also be used. For example, when the master control 700 is stationary and a zero velocity reading is measured, a duty cycle is forwarded to the motors, the duty cycle having a magnitude corresponding to the required frictional compensating force and having a 50% distribution. Thus, when an external force is applied to the hand control by the surgeon in a specific direction, a friction compensating force is delivered 50% of the time to assist in initiating movement of the master control 700, thus to compensate for stiction. As movement is then induced and the velocity reading increases in a specific direction, the distribution of the cycle changes in a direction corresponding to the direction of movement of the master control. Eventually, when the master control is being moved at a velocity corresponding to a velocity reading outside the range XX, the compensating force, or torque to the motors, is distributed 100% in a direction corresponding to the direction of movement of the master control. The duty cycle has a predetermined frequency so that, irrespective of the direction of required movement induced on the master control 700 when the master control 700 is moved, e.g., by the surgeon's hand, a corresponding friction compensating force is supplied at a percentage of the time determined by the velocity reading. The effect of this is that during movement initiation, the sticking sensation is compensated for. This enables smooth precision movements to be induced on the master control without sticking, particularly at small velocities.

As mentioned, the method of compensating for friction is not limited to friction resulting from gravity compensation. In other words, gravity model might be replaced by some other controller determining torques to be applied to the motors for another purpose. The method can be used to compensate for friction per se.

Figure 19:
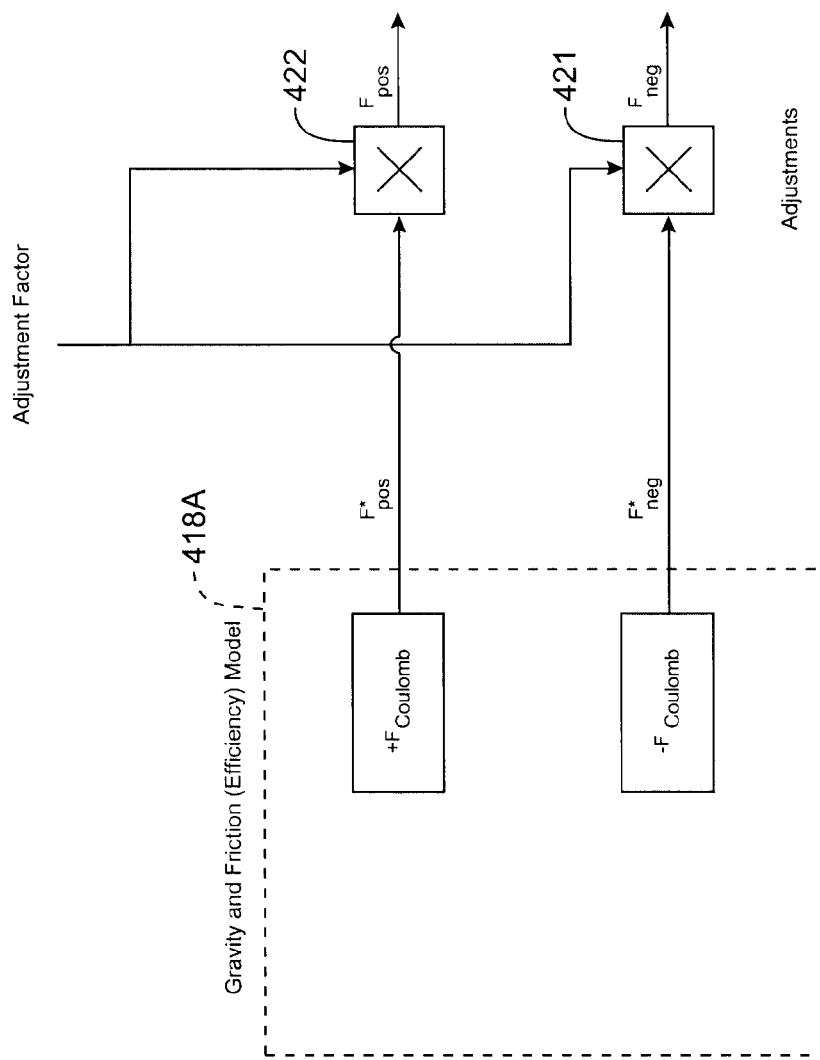
FIG. 19 shows as an alternative to FIG. 18, further detail of the algorithm shown in FIG. 17 relating to Coulomb friction compensation.

Referring now to FIG. 19, a method of compensating for friction as applied to friction per se will now be described. The method is similar to the method described above with reference to gravity compensation. However, in this case, the gravity model is replaced by a Coulomb friction model which provides a fixed compensating friction value in the arbitrary positive and negative joint movement directions. The fixed compensating friction can be set to correspond with an actual constant friction value for friction compensation as defined by actual system parameters. The adjustment factor simply may multiply these fixed values in 421 and 422. This method can be used to overcome actual friction in the joint itself, for example, should the friction in the joint require compensation. In other respects, the method of compensating for friction, and stiction, as discussed above applies. Hence, this method can be combined with the system described above or with another gravity and/or friction model using appropriate adjustments 421 and 422.

While the exemplary embodiment has been described in some detail, by way of example and for clarity of understanding, a variety of changes and modifications will be obvious to those of skill in the art. Hence, the scope of the present invention is limited solely by the appended claims.

What is claimed is:

1. A telesurgery method comprising:
    directing a surgical procedure by moving an input device of a telesurgery system with a hand of an operator;
    manipulating tissue by moving a surgical end effector in sympathy with the input device with a servomechanism of the telesurgery system;
    compensating for static friction in at least one joint of the robotic system by applying an oscillating load to the at least one joint when an absolute value of a velocity reading from the at least one joint is less than a velocity reading error range.

2. A telesurgery method as claimed in claim 1, wherein the oscillating load applying is performed by directing a duty cycle signal to an actuator drivingly coupled to the joint so that the actuator alternatingly compensates for a significant portion of the static friction of the joint in positive and negative orientations, and so that the motor does not articulate the joint when the input device is stationary.

3. A telesurgery method as claimed in claim 2, further comprising altering the duty cycle in response to the velocity reading such that the duty cycle facilitates movement of the joint toward the positive orientation when the velocity reading is positive and the duty cycle facilitates movement of the joint toward the negative orientation when the velocity reading is negative.

* * * * *